United States Patent [19]
Fleury et al.

[11] Patent Number: 5,804,580
[45] Date of Patent: Sep. 8, 1998

[54] BENZOXAZINE DERIVATIVES, METHODS FOR OBTAINING SAME, AND THEIR USE AS DRUGS

[75] Inventors: Maurice-Bernard Fleury, Neuilly Sur Seine; Jean-Marc Maurette, La Garenne Colombes; Martine Largeron, Neuilly Sur Seine, all of France

[73] Assignee: Laboratories Pharmascience, Courbevoie Cedex, France

[21] Appl. No.: 666,552

[22] PCT Filed: Dec. 29, 1994

[86] PCT No.: PCT/FR94/01557

§ 371 Date: Jul. 1, 1996

§ 102(e) Date: Jul. 1, 1996

[87] PCT Pub. No.: WO95/18114

PCT Pub. Date: Jul. 6, 1995

[30] Foreign Application Priority Data

Dec. 29, 1993 [FR] France ................................ 93 15836

[51] Int. Cl.⁶ ........................ A61K 31/535; C07D 265/36
[52] U.S. Cl. ......................................... 514/230.5; 544/105
[58] Field of Search .......................... 544/105; 514/230.5

[56] References Cited

U.S. PATENT DOCUMENTS

| | | | |
|---|---|---|---|
| 4,263,322 | 4/1981 | van't Riet et al. | 514/166 |
| 4,956,372 | 9/1990 | Kojima et al. | 514/311 |
| 5,124,325 | 6/1992 | Kojima et al. | 514/311 |

FOREIGN PATENT DOCUMENTS

| | | |
|---|---|---|
| 0310096 | 4/1989 | European Pat. Off. . |
| 0530444 | 3/1993 | European Pat. Off. . |
| 2377202 | 8/1978 | France . |
| 2504917 | 11/1982 | France . |

Primary Examiner—Richard L. Raymond
Attorney, Agent, or Firm—Greer, Burns & Crain, Ltd.

[57] ABSTRACT

Compounds are provided corresponding to the following general formula (I): in which:—$R_1$ and $R_2$, independently of each other, represent an alkyl group with 1 to 3 carbon atoms, or a group of formula —$CH_2$—$OR_a$, $R_a$ representing a hydrogen atom or a methyl group $R_x$ represents: an alkyl group with 1 to 3 carbon atoms, in particular a methyl group, or an —$OR_{x1}$ group, $R_{x1}$ representing an alkyl group with 1 to 3 carbon atoms, in particular a methoxy group, or a group of formula —$CH_2$—X in which X represents a halogen atom, in particular chlorine, or a group of formula (a)

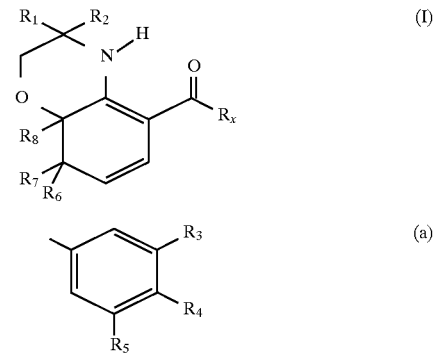

in which: $R_3$ and $R_5$, independently of each other, represent a hydrogen atom, or an —OH group, or an —$OCH_3$ group, $R_4$ represents a hydrogen atom, or an —$OR_b$ group, $R_b$ representing a hydrogen atom or a methyl group, or $R_4$ represents a group of formula —$Or_c$, $R_c$ representing a group of formula —$CH_2$—CO—$C_6H_4R'$. The present compounds are benzoxazine derivatives which are used for treating pathological conditions associated with the presence of free radicals, such as Alzheimer's disease, and methods are provided for preparation of these compounds.

23 Claims, No Drawings

BENZOXAZINE DERIVATIVES, METHODS FOR OBTAINING SAME, AND THEIR USE AS DRUGS

This application is a 371 of PCT/FR94/01557, filed Dec. 29, 1995.

The subject of the present invention is benzoxazine derivatives, as well as methods for obtaining them. The invention also relates to the pharmaceutical compositions containing these derivatives, and their uses in particular in the treatment of pathologies associated with the presence of free radicals, and more particularly of Alzheimer's disease. 2,3,4,3',4',5'-hexahydroxy benzophenone, also called Exifone, was described in the French Patent published under the number 2,257,272 and filed under the number 74 01228 on 15th Jan. 1974, as a medicament which can be used in the treatment of diseases of the capillary circulatory system.

Exifone is described in the above-mentioned French Patent amongst a group of compounds having a protective action for the catecholamines which is put to good use in the treatment of diseases of the capillary circulatory system (arteries, veins), and of diseases resulting from a hemostasis disorder and/or platelet aggregation, in particular varicose and haemorrhoid diseases. In addition, some of the compounds described in this Patent, including Exifone, are presented as possessing anti-inflammatory properties and improve capillary resistance.

Exifone has subsequently been more particularly described in the Patent published under the number 2,377,202 and filed under the number 77 00706 on 12th Jan. 1977 as a certificate of addition to the above-mentioned French Patent No. 74 01228.

Exifone is described in this certificate of addition as being able to be used in the treatment of functional deficits and metabolic disturbances which result from a cerebral and/or peripheral circulatory insufficiency. The functional deficits and metabolic disorders which may be treated by Exifone and are mentioned in particular in this certificate of addition, are the following:

* any functional symptomatology indicating a cerebral vascular insufficiency, either by vasoregulation of micro-circulation, or by improvement of cerebral oxygenation, and more particularly:
  psychic and intellectual disorders:
    change of mood,
    sleep behaviour disorders,
    lack of attention and concentration,
    memory and ideation disorders.
  sensory disorders:
    headaches, vertigo, tinnitus and hypacousia.
* sub-acute and superficial cerebral vascular troubles.
* in neurosurgery, post-concussion and post-traumatic syndromes or after-effects of surgical operations (in particular cerebral oedema).
* in ophthalmology, any affections of vascular origin:
  degenerative retinopathies (diabetes, hypertension),
  retinal spasms,
  ischemic syndromes of the fundus of the eye.
* in ENT:
  cochleovestibular syndromes: tinnitus, vertigo, Ménière's disease, hypacousia and tympanolabyrinthopexy, sclerosis,
  consequences of surgical operations and after-effects of traumatism.

More recently still, Exifone was described as being active in the treatment of Alzheimer's disease, notably due to its effects on the memory disorders, behaviour and dependency of patients suffering from Alzheimer-type senile dementia (Piette et al., La Revue de Gériatrie, Volume 11, No. 8, 1986).

However, the use of Exifone as a medicament encounters difficulties associated in particular with the poor solubility of Exifone in aqueous solvents, as well as its poor bioavailability, and due to strong links which form between the latter and the proteins in the body.

Furthermore, Exifone might be poorly tolerated, due in particular to a certain hepatotoxicity which might be observed in some patients.

The aim of the present invention is to provide new medicaments which can be used in the treatment of the group of pathologies mentioned above, and having an improved solubility, as well as a bioavailability superior to that of Exifone, whilst being better tolerated than the latter.

Another aim of the present invention is also to provide new processes for the preparation of these medicamnents.

The present in vention relates to the compounds corresponding to the following general formula (I):

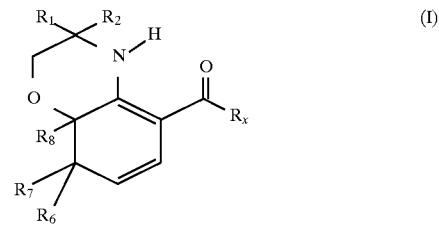

in which:

$R_1$ and $R_2$, in dependently of each other, represent an alkyl group with 1 to 3 carbon atoms, or a group of formula $—CH_2—OR_a$, $R_a$ representing a hydrogen atom or a methyl group, $R_x$ represents:
  an alkyl group with 1 to 3 carbon atoms, in particular a methyl group, or
  an $—OR_{x1}$ group, $R_{x1}$ representing an alkyl group with 1 to 3 carbon atoms, in particular a methoxy group, or
  a group of formula $—CH_2—X$ in which X represents a halogen atom, in particular chlorine, or
  a group of formula

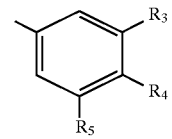

in which:
  $R_3$ and $R_5$, independently of each other, represent a hydrogen atom, or an $—OH$ group, or an $—OCH_3$ group,
  $R_4$ represents a hydrogen atom, or an $—OR_b$ group, $R_b$ representing a hydrogen atom or a methyl group, or $R_4$ represents a group of formula $—OR_c$, $R_c$ representing a group of formula $—CH_2—CO—C_6H_4R'$ in which R' represents a hydrogen atom, $—CN$ or $—OCH_3$,
  either $R_6$ represents an $—OR_d$ group, $R_d$ representing a hydrogen atom or a methyl group, when $R_7$ and $R_8$ combine to form a double bond,
  or $R_8$ represents an $—OR_e$ group in which $R_e$ represents a hydrogen atom or a methyl group, when $R_6$ and $R_7$ combine to form, with the carbon atom in position 8 of the ring, a C=O group.

A more particular subject of the invention is the compounds corresponding to the following formula (II):

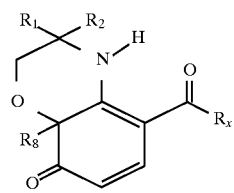

in which $R_1$, $R_2$, $R_8$ and $R_x$ are as defined above.

The invention relates more particularly to the compounds corresponding to the following formula (III):

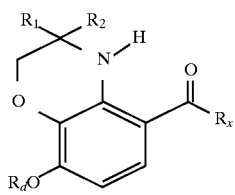

in which $R_1$, $R_2$, $R_d$ and $R_x$ are as defined above.

Also a more particular subject of the invention is the compounds corresponding to the following formula (IV):

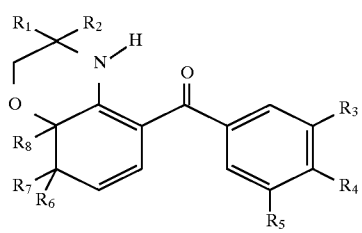

in which $R_1$ to $R_8$ are as defined above.

The invention relates more particularly still to the compounds corresponding to the following formula (V):

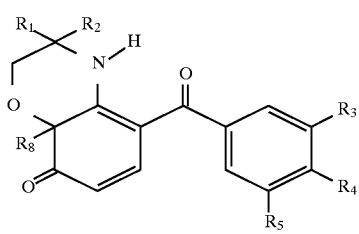

in which $R_1$ to $R_5$ and $R_8$ are as defined above.

Particularly preferred compounds of formula (V) are those corresponding to the following formulae:

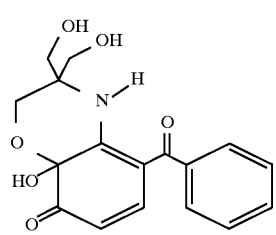
(compound no. 1)

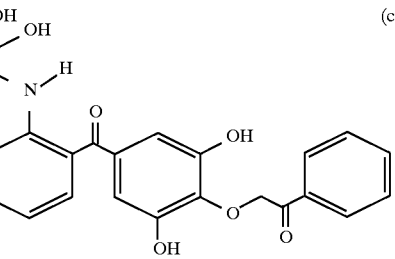
(compound no. 2)

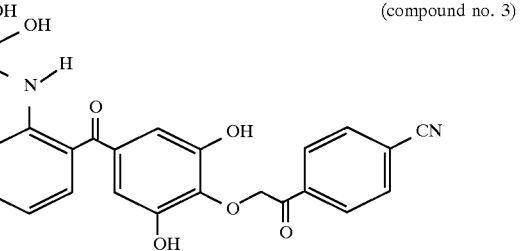
(compound no. 3)

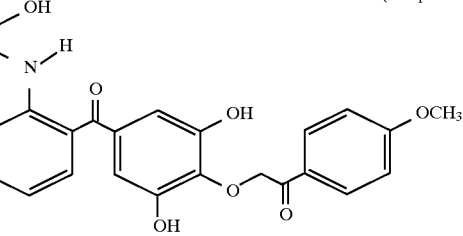
(compound no. 4)

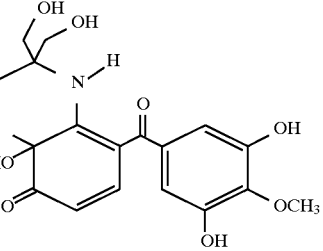
(compound no. 5)

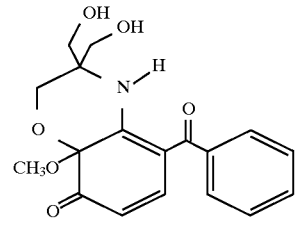
(compound no. 6)

(compound no. 7)

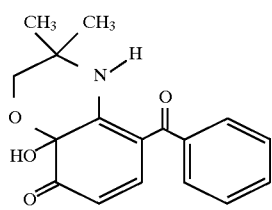
(compound no. 8)

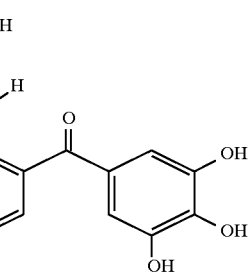
(compound no. 12)

The invention also relates more particularly to the compounds corresponding to the following formula (VI):

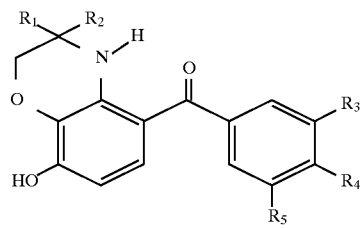
(VI)

in which $R_1$, $R_2$, $R_3$, $R_4$ and $R_5$ are as defined above.

Compounds of formula (VI) preferred within the scope of the present invention are those corresponding to the following formulae:

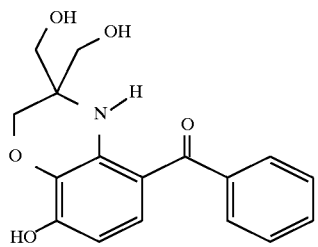
(compound no. 9)

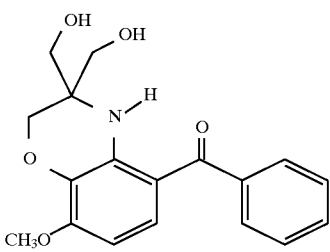
(compound no. 10)

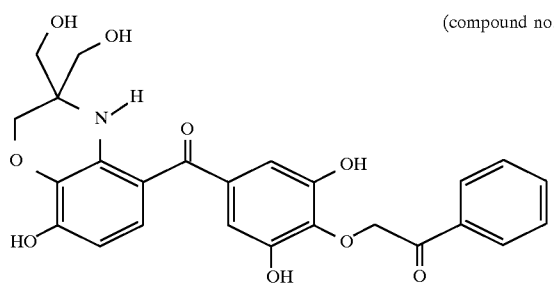
(compound no. 11)

Other preferred compounds within the scope of the present invention are those corresponding to the following formula (VII):

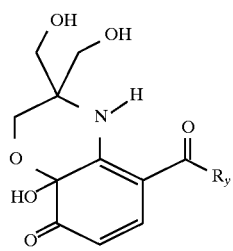
(VII)

in which $R_y$ represents:
a methyl group (compound N° 13), or
a methoxy group (compound N° 14), or
a —$CH_2Cl$ group (compound N° 15).

Also a subject of the invention is any pharmaceutical composition, characterized in that it contains, as active ingredient, at least one compound according to the invention, chosen from those described above, in combination with a pharmaceutically acceptable vehicle.

The pharmaceutical compositions according to the invention are generally presented in a form which can be administered orally, in particular in the form of tablets, or capsules, or in a form which can be administered parenterally, in particular in the form of a preparation which can be injected intravenously, intramuscularly or sub-cutaneously.

Advantageously, the daily posology for the oral forms is from about 3 mg/kg to about 20 mg/kg, preferably about 15 mg/kg, and the daily posology for the parenteral forms is from about 1 mg/kg to about 5 mg/kg.

Preferably, the unit doses of active ingredient depending on the different forms of presentation of the pharmaceutical compositions according to the invention are as follows:
oral form: about 1 mg/kg to about 10 mg/kg, advantageously about 5 mg/kg,
parenteral form: about 0.3 mg/kg to about 1 mg/kg.

The invention relates more particularly to the use of at least one compound according to the invention, to obtain a medicament intended for the treatment of affections, in particular those mentioned above, against which the benzophenones in general, and Exifone in particular, are capable of being active.

The medicaments according to the invention are more particularly intended to be used in the treatment of cognitive disorders, such as memory disorders, in particular in ageing patients.

Advantageously, the medicaments according to the invention are intended to be used in the treatment of cerebral affections which may be due to, and/or maintained, even aggravated, by the presence of free radicals in the brain, and more particularly in the treatment of Alzheimer's disease, Parkinson's disease, Trisomy 21 (Down's syndrome), schizophrenia and epilepsy.

Also a subject of the invention is the methods of preparing the above-mentioned compounds.

A method of preparing the compounds according to the invention, comprises the following stages:

a) treatment of the derivative of the following formula (VIII):

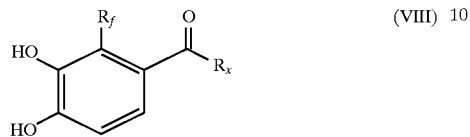

(VIII)

in which $R_f$ represents H or OH, and $R_x$ is as defined above, either chemically by bringing together said derivative of formula (VIII) and a derivative of formula $NH_2$—C$(R_1,R_2)$—$CH_2OH$ in which $R_1$ and $R_2$ are as defined above, in the presence of a metal oxide, chosen in particular from $Ag_2O$, $AgO$ and $PtO_2$, in an alcoholic, preferably methanolic, medium, or electrochemically by controlled-potential electrolysis of said derivative of formula (VIII) in the presence of a derivative of formula $NH_2$—$C(R_1,R_2)$—$CH_2OH$ as described above, in alcoholic, preferably methanolic, solution, and in the presence of a support electrolyte, chosen in particular from tetraethylammonium salts, which leads to the obtaining of a compound of the following formula (II):

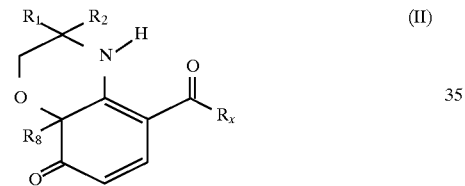

(II)

in which $R_8$ represents an —OH group, and $R_1$, $R_2$ and $R_x$ are as defined above, on condition that when $R_x$ of the derivative of the above-mentioned formula (VIII) represents a group of formula

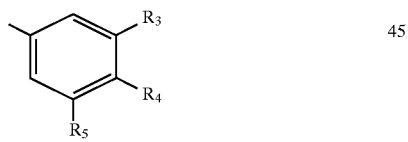

in which $R_4$ represents an —OH group, and at least one of the groups $R_3$ or $R_5$ represents an —OH group, which corresponds to the derivative of formula (VIII bis), the chemical or electrochemical treatment stage described above is preceded by a stage protecting the —OH group corresponding to $R_4$ of said derivative of formula (VIII bis), this protection stage being carried out by treatment of the derivative of formula (VIII bis) with a derivative of formula $X^1$—$CH_3$ or $X^1$—$R_c$ in which $X^1$ represents a halogen atom, in particular an iodine or bromine atom, and $R_c$ is as defined above, which leads to the obtaining of a derivative of formula (VIII ter) corresponding to a derivative of formula (VIII bis), in which at least one of $R_3$ or $R_5$ represents —OH, whilst $R_4$ represents an —$OCH_3$ or —$OR_c$ group, $R_c$ having the definition indicated above, this derivative of formula (VIII ter) then being treated by chemical or electrochemical route in the manner indicated above by a derivative of formula $NH_2$—$C(R_1,R_2)$—$CH_2OH$ in an alcohic medium, which leads to the obtaining of a compound of the above-mentioned formula (II) in which $R_8$ represents an —OH group, and $R_1$ and $R_2$ are as defined above, and $R_x$ represents a group of formula

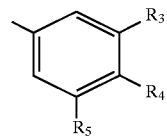

in which at least one of $R_3$ or $R_5$ represents —OH, $R_4$ represents —$OCH_3$ or —$OR_c$, $R_c$ being defined above, b) if appropriate, either alkylation of the compound of formula (II) obtained in the preceding stage a), by treatment of this compound in a basic medium with a derivative of formula $X^2$—$CH_3$, in which $X^2$ represents a halogen atom, in particular iodine, which leads to the obtaining of a compound of the above-mentioned formula (II) in which $R_8$ represents a —$OCH_3$ group, and $R_1$, $R_2$ and $R_x$ are as defined above, or reduction of the compound of formula (II) obtained in the preceding stage a):

either by chemical route by treatment of the compound of formula (II) with an acetic acid solution in the presence of Zn (advantageously about five equivalents of Zn) at ambient temperature, which leads to the obtaining of a compound of the following formula (III):

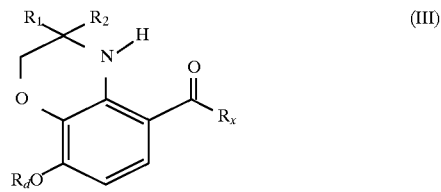

(III)

in which $R_d$ represents H, and $R_1$, $R_2$ and $R_x$ are as defined above, on condition that when the compound of the above-mentioned formula (II) is such that $R_x$ represents a group of the following formula:

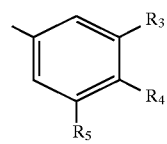

in which $R_4$ represents an —$OR_c$ group, $R_c$ being as defined above, and $R_3$ and $R_5$ being as defined above, the above-mentioned reduction by chemical route is carried out either with about five equivalents of zinc, the contact time between said compound of formula (II) and the zinc being about 2 minutes, which leads to the obtaining of a compound of the above-mentioned formula (III), in which $R_4$, in the definition of $R_x$, represents an —$OR_c$ group, $R_c$ being as defined above, and $R_3$ and $R_5$ being as defined above, or with about one hundred equivalents of zinc, the contact time between said compound of formula (II) and the zinc being about 10 minutes, or advantageously with about five equivalents of zinc, the above-mentioned contact time then being about 30 minutes, which leads, in these last two cases, to the obtaining of a compound of the above-mentioned formula (III) in which $R_4$, in the definition of $R_x$, represents an —OH group, and $R_3$ and $R_5$ being as defined above, or by electrochemical route, by controlled-potential electrolysis of the compound of the above-mentioned formula (II) in an alcoholic, preferably a methanolic, solution, in the presence of a support electolyte, chosen in particular from tetraethylammonium salts, which leads to the obtaining of the compound of the above-mentioned formula (III), on condition that when the compound of the above-mentioned formula (II) is such that $R_x$ represents a group of the following formula:

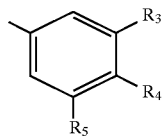

in which $R_4$ represents an —$OR_c$ group, $R_c$ being as defined above, and $R_3$ and $R_5$ being as defined above, the electrolysis potential is chosen either so as to obtain a compound of the above-mentioned formula (III), in which $R_4$, in the definition of $R_x$, represents an —$OR_c$ group, $R_c$ being as defined above, and $R_3$ and $R_5$ being as defined above (said electrolysis potential advantageously being chosen between −0.9 V e.c.s. and −1.1 V e.c.s.), or so as to obtain a compound of the above-mentioned formula (III) in which $R_4$, in the definition of $R_x$, represents an —OH group, and $R_3$ and $R_5$ being as defined above (said electrolysis potential then advantageously being chosen between −1.3 V e.c.s. and −1.6 V e.c.s.), c) if appropriate, alkylation of the compound of formula (III) obtained in the preceding Stage b), by treatment of this compound in a basic medium with a derivative of formula $X^3$—$CH_3$, in which $X^3$ represents a halogen atom, in particular iodine, which leads to the obtaining of a compound of the above-mentioned formula (III) in which $R_d$ represents an —$OCH_3$ group, and $R_1$, $R_2$ and $R_x$ are as defined above.

With regard to the starting derivatives of formula (VIII) of the above-described process for obtaining the compounds of the invention, these derivatives can be obtained, when the $R_x$ group in formula (VIII) represents a group of formula:

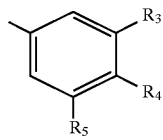

in which $R_3$, $R_4$ and $R_5$, independently of each other, represent hydrogen atoms, or an —ORg group, Rg representing a hydrogen atom or a methyl group, by reaction of an aromatic carboxylic acid, whose nucleus is substituted or not by hydroxyl groups, on phenols in the presence of catalysts such as anhydrous aluminium chloride (Friedel and Crafts' reaction), anhydrous zinc chloride on its own or with phosphorus oxychloride, boron trifluoride, by the so-called Fries reaction, in particular according to the following reaction diagram:

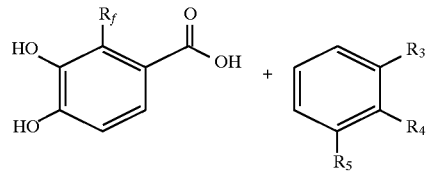

$R_f$ representing H or OH, $R_3$, $R_4$ or $R_5$ being as defined above, one of $R_3$, $R_4$ or $R_5$ obligatorily representing OH,

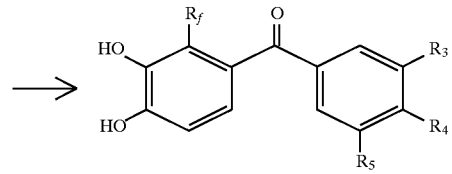

or according to the following reaction diagram:

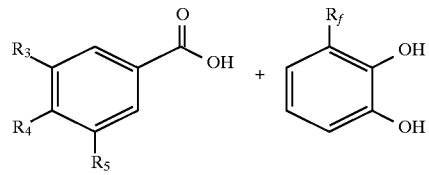

$R_f$, $R_3$, $R_4$ or $R_5$ independently of each other representing H or an —OH group,

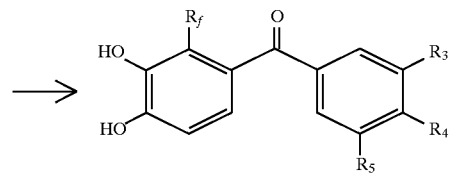

Methods for preparing the derivatives of the above-mentioned formula (VIII) are described in more detail in the French Patent No. 2,257,272 mentioned above, or also in the detailed description which follows of the invention.

With regard to the derivatives of the above-mentioned formula (VIII), in which $R_f$ represents H or an —OH group, and $R_x$ represents an alkyl group with 1 to 3 carbon atoms, in particular a methyl group, or a group of formula —$CH_2$—$X^4$ in which $X^4$ represents a halogen atom, in particular chlorine, they are either commercial products, available in particular from Aldrich, or products whose synthesis is indicated in the detailed description which follows of the invention.

Finally, with regard to the derivatives of the above-mentioned formula (VIII) in which $R_f$ represents H or an —OH group, and $R_x$ represents an —$OR_{x1}$ group, $R_{x1}$ representing an alkyl group with 1 to 3 carbon atoms, in particular a methoxy group, these latter are obtained by esterification of the derivatives of formula:

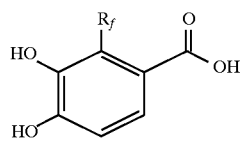

in which $R_f$ represents H or an —OH group (marketed by Aldrich), more particularly by treatment of these last-named derivatives with a compound of formula $X^5$—$R_{x1}$, $R_{x1}$ being as defined above, and $X^5$ representing a halogen atom, in particular using thionyl chloride according to the method more fully described in the detailed description which follows of the invention.

The invention also relates to the new intermediate products of formula (VIII) as such.

In this respect, the invention relates more particularly to the following derivatives of formula (VIII):

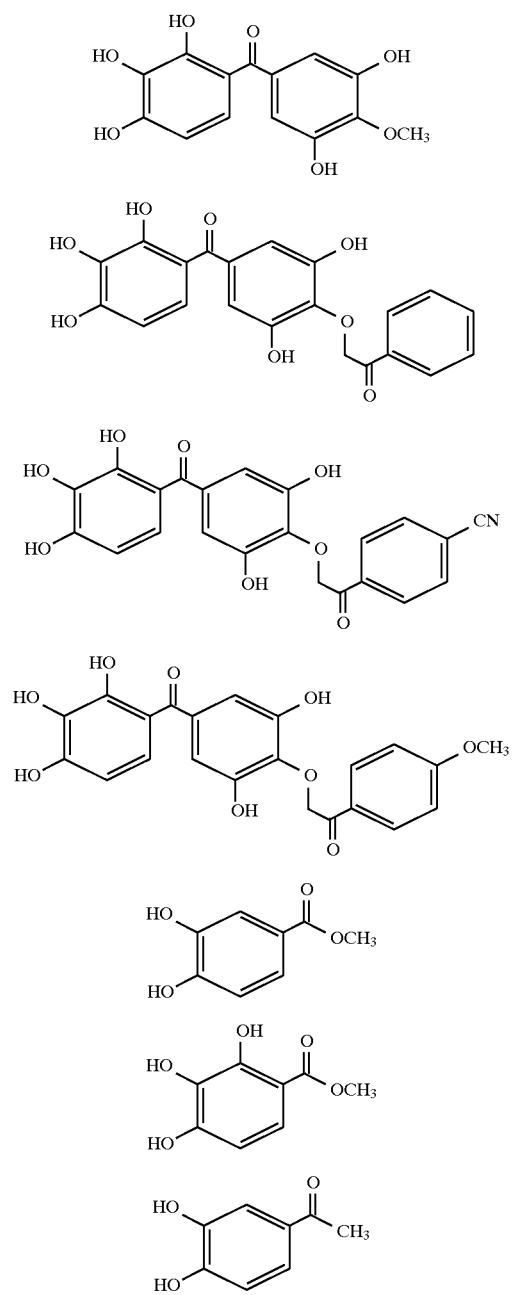

The derivatives of formula $NH_2$—$C(R_1,R_2)$—$CH_2OH$ in which $R_1$ and $R_2$ are as defined above, used in the above-mentioned process for preparing the compounds of the invention, are commercial products, available in particular from Aldrich.

The present invention will be further illustrated with the help of the examples which follow, given in a non-limitative way, of the preparation of compound of the invention and the pharmacological study carried out using some of these compounds.

I. Examples of the preparation of compounds according to the invention

In these examples, the NMR spectra were produced at 300 MHz (proton spectrum) and 75 MHz (carbon 13 spectrum) in deuterodimethylsulphoxide using a Brüker AC 300 spectrometer; the chemical shifts are expressed in ppm and the coupling constants in Hertz; s designates a singlet, d a doublet, t a triplet, dd a double doublet, and m a multiplet. The mass spectra were recorded on a Nermag R10–10C spectrometer (Chemical Ionisation, reactant gas: ammonia). The column chromatographies were carried out at atmospheric pressure using a silica with a granulometry of 40–63 μm. The melting points were determined by means of a bar-type multipoint tester.

A) Synthesis of the compounds of general formula (VIII).

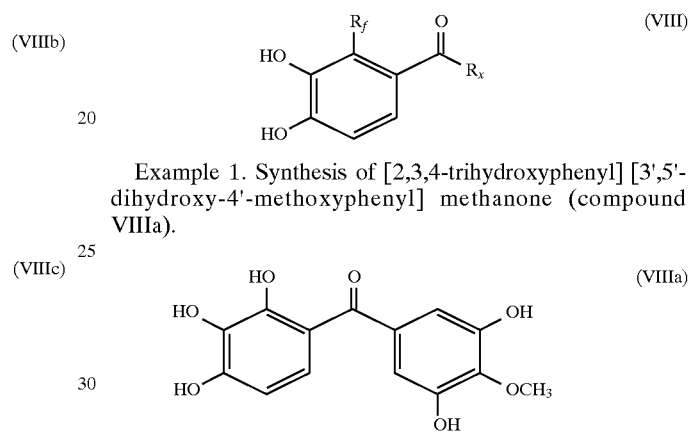

Example 1. Synthesis of [2,3,4-trihydroxyphenyl] [3',5'-dihydroxy-4'-methoxyphenyl] methanone (compound VIIIa).

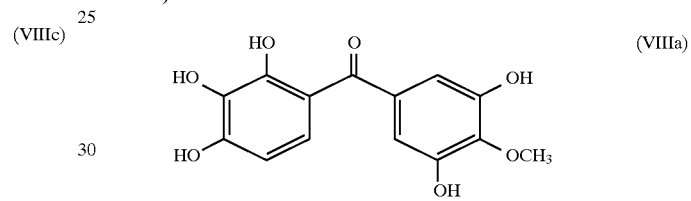

3.0 g of lithium carbonate then 30 cm³ of methyl iodide are added to a solution of 5.0 g of [2,3,4-trihydroxyphenyl] [3',4',5'-trihydroxyphenyl] methanone in 25 cm³ of dimethyl-formamide maintained at 25° C., under a nitrogen atmosphere. The reaction mixture is then stirred for twenty hours at 25° C. Then 500 cm³ of a molar aceto-acetic buffer solution are added the pH of which is about 4.50. The resultant solution is extracted with 800 cm³ of ethyl acetate. The combined organic phases are washed with 300 cm³ of distilled water, then dried over anhydrous sodium sulphate. After filtration, then evaporation to dryness under reduced pressure (2.7 kPa) at 40° C. of the ethyl acetate, 4.5 g of a residue is obtained and purified by chromatography on a fritted disc which contains 25 g of silica gel [eluant: dichloromethane/acetone, (90/10 by volume)], collecting 15 cm³ fractions. The fractions containing the mixture of the two monomethylated derivatives in position -4 and -4', are concentrated to dryness under reduced pressure (2.7 kPa), at a temperature close to 40° C. After crystallization from a dichloromethane/acetone mixture (95/5 in volumes), 1.1 g of [2,3,4-trihydroxyphenyl] [3',5'-dihydroxy-4'-methoxyphenyl] methanone is obtained in the form of a pale yellow powder melting at around 205° C. (with decomposition).

$^1$H NMR spectrum: δ 3.75 (s, 3H, $OCH_3$); 6.40 [d, 1H, H(5), J=9 Hz]; 6.60 [s, 2H, H(2') and H(6')]; 7.00 [d, 1H, H(6), J=9 Hz]; 8.70 [s, 1H, OH(3), $D_2O$ exchange]; 9.50 [s, 2H, OH(3') and OH(5'), $D_2O$ exchange]; 10.30 [s, 1H, OH(4), $D_2O$ exchange]; 12.00 [s, 1H, OH(2), $D_2O$ exchange].

$^{13}$C NMR spectrum: δ 60.8 ($OCH_3$); 108.5 [CH(5)]; 109.6 [CH(2') and CH(6')]; 113.8 (C-1); 125.9 [CH(6)]; 133.7 (C-3); 134.2 (C-4'); 139.6 (C-1'); 151.5 (C-3' and C-5'); 153.2 and 153.4 (C-2 and C-4); 200.00 (CO, methanone).

Mass spectrum (C.I.): m/z=293 ($MH^+$).

Example 2. Synthesis of [2,3,4-trihydroxyphenyl][3',5'-dihydroxy-4'-(2-oxo-2-phenylethoxy)phenyl] methanone (compound VIIIb).

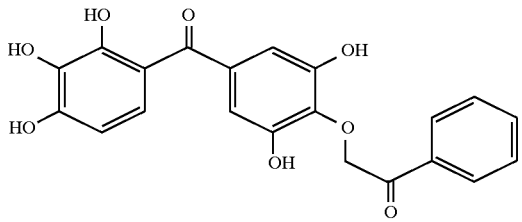
(VIIIb)

3.0 g of lithium carbonate then 3.5 g of ω-bromoacetophenone are added to a solution of 5.0 g of [2,3,4-trihydroxyphenyl] [3',4',5'-trihydroxyphenyl] methanone in 20 cm³ of dimethyl-formamide maintained at 50° C., under a nitrogen atmosphere. The reaction mixture is then agitated for 6 hours at 50° C. Then 400 cm³ of a molar aceto-acetic buffer solution, the pH of which is about 4.50, are added. The resultant solution is extracted with 800 cm³ of ethyl acetate. The combined organic phases are washed with 300 cm³ of distilled water, then dried over anhydrous sodium sulphate. After filtration then evaporation to dryness under reduced pressure (2.7 kPa) at 40° C. of the ethyl acetate, 9 g of a residue are obtained and purified by chromatography on a fritted disc which contains 50 g of silica gel [eluant: dichloromethane/acetone (90/10 by volume)], collecting 30 cm³ fractions. The fractions containing the mixture of monoacetylated derivatives in position -4 and -4' are concentrated to dryness under reduced pressure (2.7 kPa), at a temperature close to 40° C. After crystallization from a dichloromethane/acetone mixture (98/2 by volume), 2.6 g of [2,3,4-trihydroxyphenyl] [3',5'-dihydroxy-4'-(2-oxo-2-phenyl-ethoxy)-phenyl] methanone is obtained in the form of a yellow powder melting at around 180° C. (with decomposition).

$^1$H NMR spectrum: δ 4.00 (d, 1H, CH$_2$, J=12 Hz); 4.10 (d, 1H, CH$_2$, J=12 Hz); 6.40 [d, 1H, H(5), J=9 Hz]; 6.75 [d, 1H, H(2') or H(6'), J=1.7 Hz]; 6.80 [d, 1H, H(2') or H(6'), J=1.7 Hz]; 7.02 [d, 1H, H(6), J=9 Hz]; 7.40 to 7.60 [m, 5H, aromatics (phenylethoxy)]; 8.70 [s, 1H, OH(3), D$_2$O exchange]; 9.70 [s, 2H, OH(3') and OH(5'), D$_2$O exchange]; 10.20 [s, 1H, OH(4), D$_2$O exchange]; 12.60 [s, 1H, OH(2), D$_2$O exchange].

$^{13}$C NMR Spectrum: δ 71.3 (CH$_2$); 95.2 (Cq, phenylethoxy); 108.6 [CH(5)]; 110.9 [CH(2') and CH(6')]; 114.1 (C-1); 125.7 [CH(6)]; 127.5 [CH(meta), phenylethoxy]; 129.4 [CH(ortho), phenylethoxy]; 130.0 [CH(para), phenylethoxy]; 131.4(C-4'); 133.8 (C-3); 135.9 (C-1'), 141.0 and 143.5 (C-3' and C-5'), 147.0 (ketone, phenylethoxy); 153.0 (C-2 and C-4); 199.0 (CO, methanone).

Mass spectrum (C.I.):m/z=397 (MH$^+$)

Example 3. Synthesis of [2,3,4-trihydroxyphenyl][3',5'-dihydroxy-4'-(2-oxo-2-p.cyanophenylethoxy)phenyl] methanone (compound VIIIc).

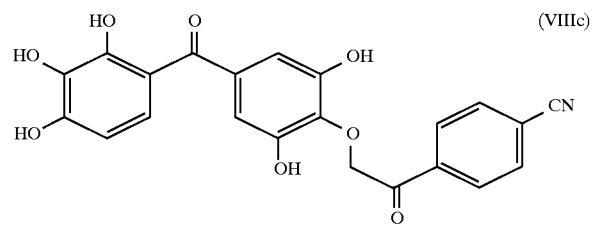
(VIIIc)

Operating as in Example 2, but replacing the ωbromoacetophenone with 4.0 g of ω-bromo-4-methoxyacetophenone, and after chromatography on a fritted disc, 3.0 g of a mixture of mono-acetylated derivatives in position -4 and -4' are obtained. A recrystalliza-tion from acetone allows 2.0 g of [2,3,4-trihydroxyphenyl][3',5'-dihydroxy-4'-(2-oxo-2-p.cyanophenylethoxy)phenyl] methanone to be isolated in the form of a pale yellow powder melting above 280° C.

$^1$H NMR spectrum: δ 4.05 (d, 1H, CH$_2$, J=12 Hz); 4.25 (d, 1H, CH$_2$, J=12 Hz); 6.40 [d, 1H, H(5), J=9 Hz]; 6.70 and 6.75 [s, 2H, H(2') and H(6')]; 7.00 [d, 1H, H(6), J=9 Hz); 7.80 [d, 2H, CH (in γ of the CN), p.cyanophenylethoxy, J=9 Hz); 7.95 [d, 2H, CH (in β of the CN), p.cyanophenylethoxy, J=9 Hz]; 8.70 [s, 1H, OH(3), D$_2$O exchange]; 9.80 [s, 2H, OH(3') and OH(5'), D$_2$O exchange]; 10.20 [s, 1H, OH(4) D$_2$O exchange]; 11.90 [s, 1H, OH(2), D$_2$O exchange].

$^{13}$C NMR Spectrum: δ 70.7 (CH$_2$); 94.9 [Cq (in δ of the CN), p.cyanophenylethoxy]; 108.5 [CH(5)]; 110.7 and 111.0 [CH(2') and CH(6')]; 112.9 [Cq (in a of the CN), p.cyanophenylethoxy]; 114.1 (C-1); 119.6 (CN); 125.7 [CH (6)]; 128.6 [CH (in γ of the CN), p.cyanophenylethoxy]; 131.5 (C-4'); 133.5 [CH (in β of the CN), p.cyanophenylethoxy]; 133.8 (C-3); 135.7 (C-1); 143.1 (CO, p.cyanophenylethoxy); 146.0 and 147.0 (C-3' and C-5'); 153.0 and 153.2 (C-2 and C-4); 199.0 (CO, methanone).

Mass spectrum (C.I.): m/z=422 (MH$^+$)

Example 4. Synthesis of [2,3,4-trihydroxyphenyl][3',5'-dihydroxy-4'-(2-oxo-2-p.methoxyphenylethoxy)phenyl] methanone (compound (VIIId).

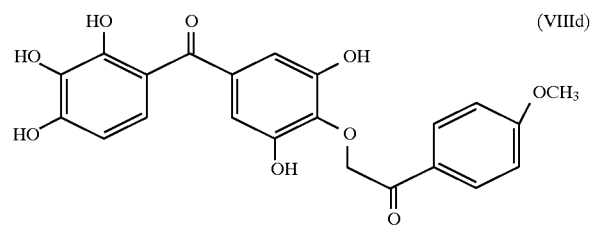
(VIIId)

Operating as in Example 2, but replacing the ω-bromoacetophenone with 4.1 g of ω-bromo-4-methoxyacetophenone and after chromatography on a fritted disc, 3.0 g of a mixture of mono-acetylated derivatives in position -4 and -4' is obtained. A recrystallization from a dichloromethane/acetone mixture (90/10 by volume) allows 2.0 9 of [2,3,4-trihydroxyphenyl][3',5'-dihydroxy-4'-(2-oxo-2-p.methoxyphenylethoxy)phenyl] methanone to be isolated in the form of a pale yellow powder.

$^1$H NMR spectrum: δ 3.75 (OCH$_3$); 3.95 (d, 1H, CH$_2$, J=12 Hz); 4.15 (d, 1H, CH$_2$, J=12 Hz); 6.40 [d, 1H, H(5), J=9 Hz]; 6.70 and 6.75 [s, 2H, H(2') and H(6')]; 6.95 [d, 2H, H (in β of the OCH$_3$), p.methoxyphenylethoxy]; 7.00 [d, 1H, H(6), J=9 Hz]; 7.50 [d, 2H, H (in γ of the OCH$_3$), p.methoxyphenylethoxy, J=9 Hz]; 8.75 [s, 1H, OH(3), D$_2$O exchange]; 9.70 [s, 2H, OH(3') and OH(5'), D$_2$O exchange]; 10.10 [s, 1H, OH(4), D$_2$O exchange]; 12.00 [s, 1H, OH(2), D$_2$O exchange].

Mass spectrum (C.I.): m/z=427 (MH⁺).

Example 5. Synthesis of methyl 3,4-dihydroxyphenyl-1-carboxylate (compound VIIIe).

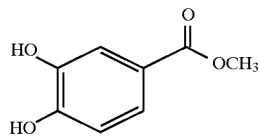
(VIIIe)

0.85 g of thionyl chloride is added to a solution of 1.00 g of 3,4-dihydroxybenzoic acid in 5 cm³ of methanol. The reaction mixture is then agitated for five hours at 60° C. The methanol is then evaporated to dryness, under reduced pressure (2.7 kPa), at a temperature close to 40° C. The residue is taken up in 20 cm³ of a molar aceto-acetic buffer solution the pH of which is about 4.5. The resultant solution is then extracted with 50 cm³ of ethyl acetate. The combined organic phases are dried over anhydrous sodium sulphate, then filtered. The ethyl acetate is evaporated to dryness under reduced pressure (2.7 kPa), at a temperature close to 40° C. 1.0 g of methyl 3,4-dihydroxyphenyl-1-carboxylate is obtained in the form of a white powder melting at around 140° C.

¹H NMR spectrum: δ 3.8 (s, 3H, CH₃); 6.8 [d, 1H, H(5), J=8 Hz]; 7.3 [dd, 1H, H(6), J=8 Hz, J=2 Hz]; 7.4 [d, 1H, H(2), J=2 Hz]; 9.6 [broad s, 2H, OH(3) and OH(4), D₂O exchange].

¹³C NMR spectrum: δ 52.7 (CH₃); 116.4 and 117.4 [CH(2) and CH(5)]; 121.6 (C-1); 122.9 [CH(6)]; 146.2 (C-3); 151.5 (C-4); 167.3 (CO, methyl carboxylate).

Mass spectrum (C.I.): m/z=169 (MH⁺).

Example 6. Synthesis of methyl 2,3,4-trihydroxyphenyl-1-carboxylate (compound VIIIf)

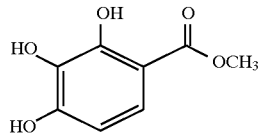
(VIIIf)

The procedure is analogous to that described in Example 5, but starting with 1.0 g of 2,3,4-trihydroxybenzoic acid and 0.8 g of thionyl chloride. 0.8 g of methyl 2,3,4-trihydroxyphenyl-1-carboxylate is obtained in the form of a white powder melting at around 160° C.

¹H NMR specrum: δ 3.8 (s, 3H, CH₃); 6.8 [d, 1H, H(5), J=9 Hz]; 7.2 [d, 1H, H(6), J=9 Hz]; 8.6 and 9.9 [broad s, 2H, OH(3) and OH(4), D₂O exchange]; 10.7 [broad s, 1H, OH(2), D₂O exchange].

¹³C NMR spectrum: δ 53.2 (CH₃); 105.5 (C-1); 108.9 [CH(5)]; 121.8 [CH(6)]; 133.7 (C-3); 152.0 and 152.9 (C-2 and C-4); 171.2 (CO, methyl carboxylate).

Mass spectrum (C.I.): m/z=185 (MH⁺).

Example 7. Synthesis of 3,4-dihydroxyacetophenone (compound VIIIg)

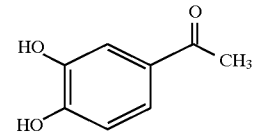
(VIIIg)

The potentially-controlled electrolysis of 200 cm³ of a hydroalcoholic solution (molar aceto-acetic buffer, pH 4.5/methanol, 50/50 by volume), of 0.47 g of ω-chloro-3,4-dihydroxyacetophenone is carried out under a nitrogen atmosphere, at 25° C., with a mercury electrode whose potential is fixed at −1.0 V e.c.s. At the end of the electrolysis, when the intensity of the current has become negligible (0.5 mA) compared with the intensity of the initial current (70 mA), the solution is then concentrated to 100 cm³, under reduced pressure (2.7 kPa), at a temperature close to 40° C. The resultant solution is extracted with 250 cm³ of ethyl acetate. The combined organic phases are dried over anhydrous sodium sulphate, filtered and the solvent is evaporated to dryness, under reduced pressure (2.7 kPa), at a temperature close to 40° C. 0.36 g of 3,4-dihydroxyacetophenone is then obtained in the form of a white powder melting at around 120° C.

¹H NMR spectrum: δ 2.5 (s, 3H, CH₃); 6.8 [d, 1H, H(5), J=9 Hz]; 7.3 [s, 1H, H(2)]; 7.4 [d, 1H, H(6), J=9 Hz]; 9.0 [broad s, 2H, OH(3) and OH(4), D₂O exchange].

¹³C NMR spectrum: δ 27.3 (CH₃); 116.0 and 116.1 [CH(2) and CH(5)]; 122.8 [CH(6)]; 130.0 (C-1); 146.3 (C-3); 151.9 (C-4), 197.0 (CO, acetophenone).

Mass spectrum (C.I.): m/z=153 (MH⁺).

B) Synthesis of the compounds of general formula II.

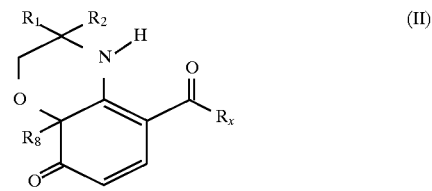
(II)

Example 8. Synthesis of (RS)-5-benzoyl-3,3-bis (hydroxymethyl)-8a-hydroxy-3,4-dihydro-2H-1,4-benzoxazin-8(8aH)-one (compound N° 1).

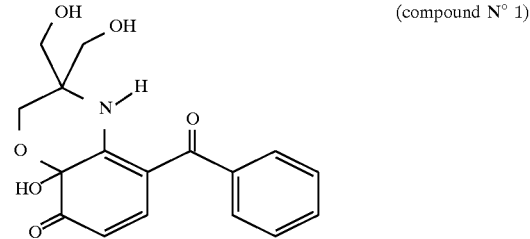
(compound N° 1)

a) Synthesis by chemical route 0.46 g of 2,3,4-trihydroxybenzophenone is dissolved in 1 litre of a methanolic solution containing 12.10 g of TRIS, agitated under a nitrogen atmosphere, at ambient temperature. 2.30 g of silver oxide (Ag₂O) are then added. The reaction mixture is agitated for 2 hours, then filtered; the methanol is then evaporated to dryness, under reduced pressure (2.7 kPa), at a temperature close to 40° C. The residue is taken up in 200 cm³ of a molar aceto-acetic buffer solution, the pH of which is about 4.50. The resultant solution is then extracted with 400 cm³ of ethyl acetate. The combined organic phases are dried over anhydrous sodium sulphate, then filtered; the ethyl acetate is evaporated to dryness under reduced pressure (2.7 kPa), at a temperature close to 40° C. The residue is taken up in 2 cm³ of ethyl acetate and the solution obtained is placed on a 20 g silica gel column (diameter: 1.8 cm, height 60 cm). The column is eluted with an ethyl acetate/methanol mixture (98/2 by volume), collecting 5 cm³ fractions. The fractions containing the expected product are concentrated to dryness under reduced pressure (2.7 kPa), at a temperature close to 40° C. 0.53 g of (RS)-5-benzoyl-3,3-bis (hydroxymethyl)-8a-hydroxy-3,4-dihydro-2H-1,4-benzoxazin-8(8aH)-one is obtained in the form of an orange powder, melting at around 170° C. (with decomposition).

¹H NMR spectrum: δ 3.40 [dd, 1H, CH₂OH(3), J=12 Hz, J=5 Hz]; 3.50 [d, 2H, CH₂OH(3), J=5 Hz]; 3.60 [dd, 1H, CH₂OH(3), J=12 Hz, J=5 Hz]; 3.85 [d, 1H, CH₂(2), J=12 Hz]; 4.20 [d, 1H, CH₂(2), J=12 Hz]; 5.20 [d, 1H, H(7), J=10 Hz]; 5.40 [m, 2H, OH (alcohol), D₂O exchange]; 7.20 [d, 1H, H(6), J=10 Hz], 7.50 [m, 5H, aromatics, benzoyl(5)]; 8.30 [s, 1H, OH(8a), D₂O exchange]; 12.30 [s, 1H, NH, D₂O exchange].

¹³C NMR spectrum: δ 56.5 (C-3); 58.3 [CH₂(2)]; 60.7 [CH₂OH(3)], 61.2 [CH₂OH(3)]; 86.6 (C-8a); 98.8 (C-5); 107.7 [CH(7)]; 127.5 [CH(meta), benzoyl(5)]; 128.2 [CH (ortho), benzoyl(5)]; 130.0 [CH(para), benzoyl(5)]; 139.4 [Cq, benzoyl(5)], 146.0 [CH(6)]; 167.1 (C-4a); 190.0 [CO (8)]; 192.6 [CO, benzoyl(5)].

Mass spectrum (C.I.): m/z=332 (MH⁺).

b) synthesis by electrochemical route b-1) The potentially-controlled electrolysis is carried out by means of a three-electrode assembly. The electrolysis cell consists of a set of ground glassware, the anode and cathode compartments being concentric and separated by a fritted glass wall with a porosity of 7. A Tacussel PJT 120V-1A potentiostat-galvanostat and a Tacussel IG6N integrator complete the circuit.

The work electrode is a 10% irradiated platinum gauze, 25 mm high and with an inner diameter of 60 mm. The auxiliary electrode is a platinum foil. The reference electrode is a calomel electrode in a saturated solution of potassium chloride (e.c.s.).

The electrolysis of a solution of 0.115 g of 2,3,4-trihydroxy benzophenone in 250 cm³ of methanol containing 3.020 g of Tris and 1.150 g of tetraethylammonium perchlorate as the electrolyte support is carried out, under a nitrogen atmosphere, at 25° C., with a platinum electrode whose potential is fixed at +0.4V e.c.s. At the end of the electrolysis, when the intensity of the current has become negligible (0.5 mA) compared with the intensity of the initial current (60 mA), the resultant solution is evaporated to dryness under reduced pressure (2.7 kPa) at a temperature close to 40° C. The residue is taken up in 100 cm³ of a molar aceto-acetic buffer solution the pH of which is about 4.5. The resultant solution is then extracted with 200 cm³ of ethyl acetate. The combined organic phases are dried over anhydrous sodium sulphate, filtered and the solvent evaporated to dryness under reduced pressure (2.7 kPa), at a temperature close to 40° C. The residue is then taken up in 1 cm³ of ethyl acetate and the solution obtained is placed on a 10 g silica gel column (diameter 1.3 cm, height 60 cm). The column is eluted with an ethyl acetate/methanol mixture (98/2 by volume), collecting 2 cm³ fractions. The fractions containing the expected product are concentrated to dryness under reduced pressure (2.7 kPa), at a temperature close to 40° C. 0.12 g of compound No. 1 is obtained whose characteristics are identical to those of the product obtained in paragraph a) above.

b-2) Operating as in paragraph b-1) above, but replacing the platinum electrode with a layer of mercury the potential of which is fixed at 0.0 V e.c.s., the electrolysis of 0.115 g of 2,3,4-trihydroxybenzophenone is carried out. 0.100 g of compound No. 1 is obtained whose characteristics are identical to those of the product obtained in paragraph a) above.

b-3) Compound No. 1 can also be obtained by operating as in paragraph b-1) above, but starting with 0.11 g of 3,4-dihydroxy-benzophenone. In this way 0.08 g of compound No. 1 is obtained whose characteristics are identical to those of the product obtained in paragraph a) above.

Example 9. Synthesis of (RS)-5-[3,5-dihydroxy-4-(2-oxo-2-phenylethoxy)]-benzoyl-3,3-bis(hydroxymethyl)-8a-hydroxy-3,4-dihydro-2H-1,4-benzoxazin-8(8aH)-one (compound No. 2).

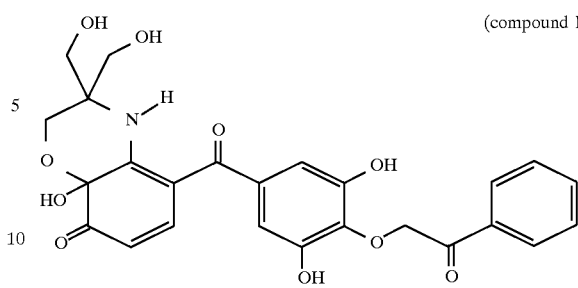
(compound N° 2)

The procedure is analogous to that described in Example 8a), but starting with 0.79 g of [2,3,4-trihydroxy-phenyl][3', 5'-dihydroxy-4'-(2-oxo-2-phenylethoxy)phenyl] methanone (compound VIIIb described in Example 2), 12.10 g of Tris and 2.30 g of silver oxide (Ag₂O). After purification by chromatography on a 30 g silica gel column (diameter: 2.0 cm, height: 60 cm) eluted with an ethyl acetate/methanol mixture (97/3 by volume), 0.40 g of (RS)-5-[3,5-dihydroxy-4-(2-oxo-2-phenylethoxy)-benzoyl]-3,3-bis(hydroxymethyl)-8a-hydroxy-3,4-dihydro-2H-1,4-benzoxazin-8(8aH)-one is obtained in the form of an orange powder melting at around 185° C. (with decomposition).

¹H NMR spectrum: δ 3.40 [dd, 1H, CH₂OH(3), J=12 Hz, J=5 Hz]; 3.50 [d, 2H, CH₂OH(3), J=5 Hz]; 3.60 [dd, 1H, CH₂OH(3), J=12 Hz, J=5 Hz]; 3.85 [d, 1H, CH₂(2), J=12 Hz]; 3.90 [dd, 1H, CH₂(phenylethoxy), J=12 Hz, J=5 Hz]; 4.20 [d, 2H, CH₂(phenylethoxy) and CH₂(2), J=12 Hz]; 5.20 [dd, 1H, H(7), J=10 Hz, J=2 Hz]; 5.35 [m, 2H, OH(alcohol), D₂O exchange]; 6.55 [m, 2H, H(2) and H(6), benzoyl(5)]; 7.30 [dd, 1H, H(6), J=10 Hz, J=2 Hz]; 7.40 to 7.60 [m, 5H, aromatics, phenylethoxy]; 8.30 [s, 1H, OH(8a), D₂O exchange]; 9.60 [s, 2H, OH(3) and OH(5), benzoyl(5), D₂O exchange]; 12.10 [s, 1H, NH, D₂O exchange]. ¹³C NMR spectrum: δ 57.7 (C-3); 59.5 [CH₂(2)]; 61.9 [CH₂OH(3)], 62.4 [CH₂OH(3)]; 71.3 [CH₂(phenylethoxy)]; 88.0 (C-8a); 95.2 [Cq(phenylethoxy)]; 99.9 (C-5); 108.3 [CH(7)]; 109.3 and 109.8 [CH(2) and CH(6), benzoyl(5)]; 127.4 [CH(meta), phenylethoxy]; 129.3 [CH (ortho), phenylethoxy]; 130.2 [CH (para), phenylethoxy]; 134.5 [C-4, benzoyl(5)]; 135.7 [C-1, benzoyl(5)]; 141.1 and 143.6 [C-3 and C-5, benzoyl(5)]; 146.9 (CO, phenylethoxy); 147.7 [CH(6)]; 168.2 (C-4a); 191.4 [CO(8)]; 192.4 [CO, benzoyl(5)]. Mass spectrum (C.I.): m/z=498 (MH⁺).

Example 10. Synthesis of (RS)-5-[3,5-dihydroxy-4-(2-oxo-2-p.cyanophenylethoxy)1benzoyl-3,3-bis(hydroxymethyl)-8a-hydroxy-3,4-dihydro-2H-1,4-benzoxazin-8(8aH)-one (compound N° 3).

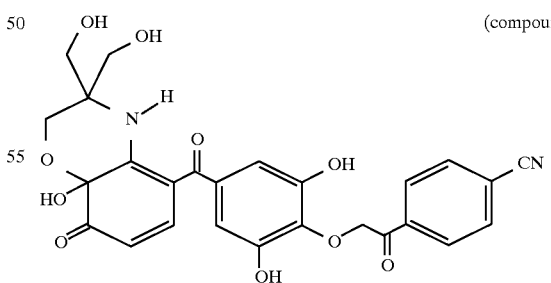
(compound N° 3)

The procedure is analogous to that described in Example 8a), but starting with 0.84 g of [2,3,4-trihydroxyphenyl][3', 5'-dihydroxy-4'-(2-oxo-2-p.cyanophenylethoxy)phenyl] methanone (compound VIIIc described in Example 3), 12.10 g of Tris and 2.30 g of silver oxide (Ag₂O). After purification by chromatography on a 30 g silica gel column (diameter 2.0 cm, height 60 cm), eluted with an ethyl acetate/methanol mixture (97/3 by volume), 0.42 g of (RS)-5-[3,5-dihydroxy-4-(2-oxo-2-p.cyanophenyl-ethoxy)]benzoyl-3,3-bis-(hydroxymethyl)-8a-hydroxy-3,4-dihydro-2H-1,4-benzoxazin-8(8aH)-one is obtained in the form of an orange powder melting at around 215° C. (with decomposition).

$^1$H NMR spectrum: δ 3.35 (d, 1H, CH$_2$OH(3), J=11 Hz); 3.50 [s, 2H, CH$_2$OH(3)]; 3.60 [d, 1H, CH$_2$OH(3), J=11 Hz]; 3.80 [d, 1H, CH$_2$(2)]; 3.90 [d, 1H, CH$_2$(p.cyanophenylethoxy)]; 4.20 [m, 2H, CH$_2$-(p.cyanophenyloxy) and CH$_2$(2)]; 5.20 [dd, 1H, H(7), J=9 Hz, J=2 Hz]; 5.35 [m, 2H, OH(alcohol), D$_2$O exchange]; 6.55 [m, 2H, H(2) and H(6), benzoyl(5)]; 7.35 [dd, 1H, H(6), J=9 Hz, J=2 Hz]; 7.75 [d, 2H, H(in γ of the CN), p.cyanophenylethoxy, J=9 Hz]; 7.95 [d, 2H, H(in β of the CN), p.cyanophenylethoxy, J=9 Hz]; 8.25 [s, 1H, OH(8a), D$_2$O exchange]; 9.70 [s, 2H, OH(3) and OH(5), benzoyl(5), D$_2$O exchange]; 12.10 [s, 1H, NH, D$_2$O exchange].

$^{13}$C NMR spectrum: δ 57.7 (C-3); 59.7 [CH$_2$(2)]; 61.9 [CH$_2$OH(3)], 62.4 [CH$_2$OH(3)]; 70.7 (CH$_2$, p.cyanophenylethoxy); 87.9 (C-8a); 94.9 [Cq(in δ of the CN), p.cyanophenylethoxy); 99.8 (C-5); 108.3 [CH(7)]; 109.2 and 109.9 [CH(2) and CH(6), benzoyl(5)]; 112.9 [Cq(in α of the CN), p.cyanophenylethoxy]; 119.7 (CN); 128.6 [CH(in γ of the CN), p.cyanophenylethoxy]; 133.0 [C-4, benzoyl(5)]; 133.5 [CH(in β of the CN), p.cyanophenylethoxy]; 134.3 [C-1, benzoyl(5)]; 143.2 (ketone, p.cyanophenylethoxy); 146.0 and 147.0 [C-3 and C-5, benzoyl(5)]; 147.7 [CH(6)]; 168.2 (C-4a); 191.4 [CO(8)]; 192.8 [CO, benzoyl(5)].

Mass spectrum (C.I.): m/z=523 (MH$^+$).

Example 11. Synthesis of (RS)-5-[3,5-dihydroxy-4-(2-oxo-2-p.methoxyphenylethoxy)]benzoyl-3,3-bis (hydroxymethyl)-8a-hydroxy-3,4-dihydro-2H-1,4-benzoxazin-8(8aH)-one (compound N° 4).

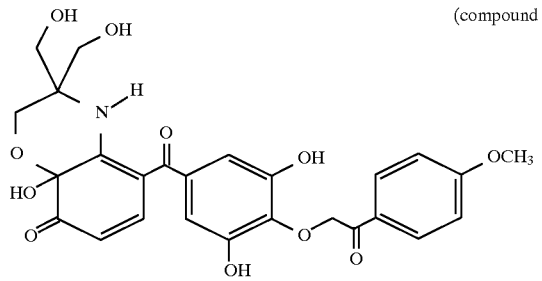
(compound N° 4)

The procedure is analogous to that described in Example 8a), but starting with 0.85 g of [2,3,4-trihydroxyphenyl][3',5'-dihydroxy-4'-(2-oxo-2-p.methoxyphenyl-ethoxy)phenyl] methanone (compound VIIId described in Example 4), 12.10 g of Tris and 2.30 g of silver oxide (Ag$_2$O). After purification by chromatography on a 30 g silica gel column (diameter 2.0 cm, height 60 cm), eluted with an ethyl acetate/methanol mixture (97/3 by volume), 0.37 g of (RS)-5-[3,5-dihydroxy-4-(2-oxo-2-p.methoxyphenyl-ethoxy)benzoyl-3,3-bis-(hydroxymethyl)-8a-hydroxy-3,4-dihydro-2H-1,4-benzoxazin-8(8aH)-one is obtained in the form of an orange powder.

$^1$H NMR spectrum: δ 3.35 [d, 1H, CH$_2$OH(3) J=11 Hz]; 3.50 [s, 2H, CH$_2$OH(3)]; 3.60 [d, 1H, CH$_2$OH(3), J=11 Hz]; 3.75 (s, 3H, OCH$_3$); 3.80 (d, 1H, CH$_2$(2), J=11 Hz]; 3.90 [d, 1H, CH$_2$(p.methoxy-phenylethoxy)]; 4.20 [m, 2H, CH$_2$-(p.methoxyphenylethoxy) and CH$_2$(2)]; 5.20 [dd, 1H, H(7), J=9 Hz, J=2 Hz]; 5.40 [broad s, 2H, OH(alcohol), D$_2$O exchange]; 6.40 to 6.60 [m, 2H, H(2) and H(6), benzoyl(5)]; 7.00 [d, 2H, H(in β of the OCH$_3$), p.methoxy-phenylethoxy, J=9 Hz]; 7.35 [dd, 1H, H(6), J=9 Hz, J=2 Hz]; 7.50 [d, 2H, H(in γ of the OCH$_3$), J=9 Hz]; 8.30 [s, 1H, OH(8a), D$_2$O exchange]; 9.65 [s, 2H, OH(3) and OH(5), benzoyl(5), D$_2$O exchange]; 12.10 [s, 1H, NH, D$_2$O exchange].

$^{13}$C NMR spectrum: δ 56.3 (OCH$_3$); 57.7 (C-3); 59.5 [CH(2)]; 61.9 [CH$_2$OH(3)], 62.4 [CH$_2$OH(3)]; 71.4 (CH$_2$, p.methoxyphenyl-ethoxy); 88.0 (C-8a); 95.2 [Cq(in δ of the OCH$_3$), p.methoxy-phenylethoxy]; 99.9 (C-5); 108.3 [CH(7)]; 114.8 and 115.2 [CH(2) and CH(6), benzoyl(5)]; 128.8 [CH(in γ of the OCH$_3$, p.methoxy-phenylethoxy]; 131.6 [CH (in β of the OCH$_3$), p.methoxyphenyl-ethoxy]; 133.2 [C-4, benzoyl(5)]; 134.5 [C-1, benzoyl(5)] 146.9 (CO, p.methoxyphenylethoxy); 147.7 [CH(6)]; 160.7 [Cq(in α of the OCH$_3$)]; 168.2 (C-4a); 191.4 [CO(8)]; 193.4 [CO, benzoyl(5)].

Mass spectrum (C.I.): m/z=528 (MH$^+$).

Example 12. Synthesis of (RS)-5-(3,5-dihydroxy-4-methoxy)-benzoyl-3,3-bis(hydroxymethyl)-8a-hydroxy-3,4-dihydro-2H-1,4-benzoxazin-8(8aH)-one (compound N° 5).

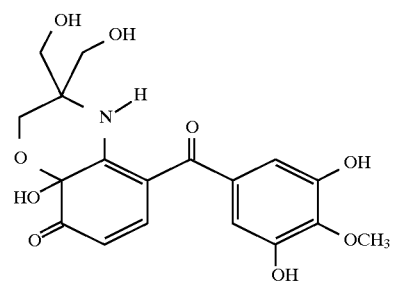
(compound N° 5)

The procedure is analogous to that described in Example 8a), but starting with 0.58 g of [2,3,4-trihydroxyphenyl][3',5'-dihydroxy-4'-methoxyphenyl] methanone (compound VIIIa described in Example 1), 12.10 g of Tris and 1.24 g of silver oxide (AgO). After purification by chromato-graphy on a 20 g silica gel column (diameter 1.8 cm, height 60 cm), eluted with an ethyl acetate/methanol mixture (95/5 by volume), 0.3 g of (RS)-5-(3,5-dihydroxy-4-methoxy)-benzoyl-3,3-bis(hydroxymethyl)-8a-hydroxy-3,4-dihydro-2H-1,4-benzoxazin-8(8aH)-one is obtained in the form of an orange powder melting at around 150° C. (with decomposition).

$^1$H NMR spectrum: δ 3.35 [d, 1H, CH$_2$OH(3), J=11 Hz]; 3.50 [s, 2H, CH$_2$OH(3)]; 3.60 [d, 1H, CH$_2$OH(3), J=11 Hz]; 3.75 (s, 3H, OCH$_3$); 3.85 [d, 1H, CH$_2$(2), J=12 Hz]; 4.20 [d, 1H, CH$_2$(2), J=12 Hz]; 5.15 [d, 1H, H(7), J=10 Hz]; 5.40 [broad s, 2H, OH(alcohol), D$_2$O exchange]; 6.40 [s, 2H, H(2) and H(6), benzoyl (5)]; 7.30 [d, 1H, H(6), J=10 Hz]; 8.25 [broad s, 1H, OH(8a), D$_2$O exchange]; 9.40 [broad s, 2H, OH(31) and OH(5'), D$_2$O exchange]; 12.10 [s, 1H, NH, D$_2$O exchange].

$^{13}$C NMR spectrum: δ 57.7 (C-3); 59.5 [CH$_2$(2)]; 60.8 (OCH$_3$); 61.9 [CH$_2$OH(3)], 62.4 [CH$_2$OH(3)]; 87.9 (C-8a); 100.0 (C-5); 108.3 [CH(7); CH(2) and CH(6), benzoyl(5)]; 135.7 [C-4, benzoyl(5)]; 138.3 [C-1, benzoyl(5)]; 147.8 [CH(6)]; 151.6 [C-3 and C-5, benzoyl(5)]; 168.2 (C-4a); 191.4 [CO(8)]; 193.5 [CO, benzoyl(5)].

Mass spectrum (C.I.): m/z=377 (MH$^+$).

Example 13. Synthesis of (RS)-5-benzoyl-3,3-bis-(hydroxy-methyl)-8a-methoxy-3,4-dihydro-2H-1,4-benzoxazin-8(8aH)-one (compound N° 6).

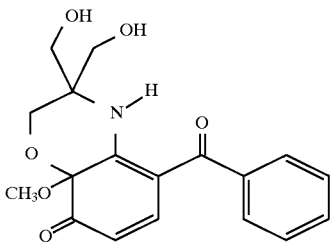

(compound N° 6)

0.027 g of sodium methylate in solution in 0.5 cm³ of methanol, then 0.5 cm³ of methyl iodide are added to a solution of 0.160 g of compound N° 1 in 2 cm³ of dimethylformamide maintained at ambient temperature, under a nitrogen atmosphere. The reaction mixture is then agitated for three hours at ambient temperature. 38 cm³ of distilled water are then added. The resultant solution is extracted with 100 cm³ of ethyl acetate. The combined organic phases are washed with 100 cm³ of distilled water, then dried over anhydrous sodium sulphate. After filtration then concentration to dryness, under reduced pressure (2.7 kPa) at 40° C. of the organic phases, 0.18 g of a residue is obtained and purified by chromatography on a 7 g silica gel column (diameter 1.3 cm, height 60 cm). The column is eluted with an ethyl acetate/methanol mixture (97/3 by volume), collecting 3 cm³ fractions. The fractions containing the expected product are concentrated to dryness under reduced pressure (2.7 kPa), at a temperature close to 40° C. 0.16 g of (RS)-5-benzoyl-3,3-bis-(hydroxymethyl)-8a-methoxy-3,4-dihydro-2H-1,4-benzoxazin-8(8aH)-one is obtained in the form of an orange powder melting at around 168° C. (with decomposition).

$^1$H NMR spectrum: δ 3.20 (s, 3H, OCH$_3$); 3.40 [dd, 1H, CH$_2$OH(3), J=12 Hz, J=5 Hz]; 3.50 [d, 2H, CH$_2$OH(3), J=5 Hz]; 3.65 [dd, 1H, CH$_2$OH(3), J=12 Hz, J=5 Hz]; 3.95 [s, 2H, CH$_2$(2)]; 5.20 [d, 1H, H(7), J=10 Hz]; 5.40 [m, 2H, OH(alcohol), D$_2$O exchange]; 7.20 [d, 1H, H(6), J=10 Hz]; 7.40 to 7.50 [m, 5H, aromatics, benzoyl(5)]; 12.30 (s, 1H, NH, D$_2$O exchange).

$^{13}$C NMR spectrum: δ 51.0 (OCH$_3$); 57.0 (C-3); 59.5 [CH$_2$(2)]; 61.5 [CH$_2$OH(3)]; 62.0 [CH$_2$OH(3)]; 90.0 (C-8a); 100.0 (C-5); 108.0 [CH(7)]; 128.0 [CH(meta), benzoyl(5)]; 129.0 [CH(ortho), benzoyl(5)]; 130.8 [CH(para), benzoyl(5)]; 139.7 [Cq, benzoyl(5)]; 147.0 [CH(6)]; 166.0 (C-4a); 189.0 [CO (8)]; 193.0 [CO, benzoyl(5)]. Mass spectrum (C.I.): m/z=346 (MH$^+$).

Example 14. Synthesis of (RS)-5-benzoyl-3,3-bis-(hydroxymethyl, methyl)-8a-hydroxy-3,4-dihydro-2H-1,4-benzoxazin-8(8aH)-one (compound no. 7).

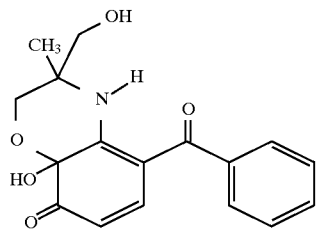

(compound no. 7)

a) Operating as in Example 8a), but replacing the TRIS with 10.5 g of 2-amino-2-methyl-propanediol, 0.38 g of (RS)-5-benzoyl-3, 3-bis-(hydroxymethyl,methyl)-8a-hydroxy-3, 4-dihydroxy-2H-1,4-benzoxazin-8(8aH) one is obtained in the form of an orange powder melting at around 155° C. (with decomposition).

This is a mixture of two diastereoisomers A and B.

$^1$H NMR spectrum of diastereoisomer A (65%): δ 1.25 [s, 3H, CH$_3$(3)]; 3.45 [s, 2H, CH$_2$OH(3)]; 3.85 [d, 1H, CH$_2$(2), J=12 Hz]; 4.15 [d, 1H, CH$_2$(2), J=12 Hz]; 5.20 [d, 1H, H(7), J=10 Hz]; 5.45 [broad s, 1H, OH(alcohol), D$_2$O exchange]; 7.20 [d, 1H, H(6), J=10 Hz]; 7.45 [m, 5H, aromatics, benzoyl(5)]; 8.40 (broad s, 1H, OH(8a), D$_2$O exchange]; 12.20 [s, 1H, NH, D$_2$O exchange].

$^{13}$C NMR spectrum of diastereoisomer A: δ 21.6 [CH$_3$(3)]; 54.7 (C-3); 62.6 [CH$_2$(2)]; 67.2 [CH$_2$OH(3)]; 87.7 (C-8a); 99.8 (C-5); 108.9 [CH(7)]; 128.7 [CH(meta), benzoyl(5)]; 129.4 [CH(ortho), benzoyl(5)]; 131.2 [CH (para), benzoyl(5)]; 140.5 [Cq, benzoyl(5)]; 147.2 [CH(6)]; 168.1 (C-4a); 191.2 [CO (8)]; 194.0 [CO, benzoyl(5)].

Mass spectrum (C.I.): m/z=316 (MH$^+$).

$^1$H NMR spectrum of diastereoisomer B (35%): δ 1.35 [s, 3H, CH$_3$(3)]; 3.47 [s, 2H, CH$_2$OH(3)]; 3.75 [d, 1H, CH$_2$(2), J=12 Hz]; 4.25 [d, 1H, CH$_2$(2), J=12 Hz]; 5.15 [d, 1H, H(7), J=10 Hz]; 5.45 [broad s, 1H, OH(alcohol), D$_2$O exchange]; 7.15 [d, 1H, H(6), J=10 Hz]; 7.45 [m, 5H, aromatics, benzoyl(5)]; 8.30 (broad s, 1H, OH(8a), D$_2$O exchange]; 12.30 [s, 1H, NH, D$_2$O exchange].

$^{13}$C NMR spectrum of diastereoisomer B: δ 24.7 [CH$_3$(3)]; 55.5 (C-3); 63.6 [CH$_2$(2)]; 66.0 [CH$_2$OH(3)]; 87.9 (C-8a); 98.8 (C-5); 108.7 [CH(7)]; 128.7 [CH(meta), benzoyl(5)]; 129.4 [CH(ortho), benzoyl(5)]; 131.2 [CH (para), benzoyl(5)]; 140.5 [Cq, benzoyl(5)]; 147.2 [CH(6)]; 166.0 (C-4a); 191.2 [CO (8)]; 194.0 [CO, benzoyl(5)].

Mass spectrum (C.I.): m/z=316 (MH$^+$).

b) Compound no. 7 can also be obtained by operating as in Example 8 b-1), but starting with 0.110 g of 3,4-dihydroxybenzo-phenone and replacing the Tris with 2.62 g of 2-amino-2-methyl-propanediol. 0.055 g of compound no. 7 is thus obtained, whose characteristics are identical to those of the product obtained in Example 14 a).

Example 15. Synthesis of (RS)-5-benzoyl-3,3-bis-(methyl)-8a-hydroxy-3, 4-dihydro-2H-1,4-benzoxazin-8 (8aH)-one (compound no. 8).

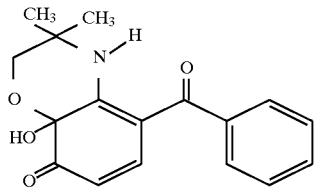

(compound no. 8)

The procedure is analogous to that described in Example 8 a), but replacing Ag$_2$O with 1.24 g of Ago and the Tris with 8,9 g of 2-amino-2-methylpropanol. After purification by chromatography on a 20 g silica gel column (diameter: 1.8 cm, height 60 cm), eluted with a dichloromethane/methanol mixture (98/2 by volume), 0.23 g of (RS)-5-benzoyl-3,3-bis-(methyl)-8a-hydroxy-3,4-dihydro-2H-1,4-benzoxazin-8 (8aH)-one is obtained in the form of an orange powder melting at around 140° C. (with decomposition).

$^1$H NMR spectrum: δ 1.35 [s, 3H, CH$_3$(3)]; 1.40 [s, 3H, CH$_3$(3)]; 3.75 [d, 1H, CH$_2$(2), J=12 Hz]; 4.20 [d, 1H, CH$_2$(2), J=12 Hz]; 5.20 [d, 1H, H(7), J=10 Hz]; 7.20 [d, 1H, H(6), J=10 Hz]; 7.50 [m, 5H, aromatics, benzoyl(5)]; 8.35 [s, 1H, OH(8a), D$_2$O exchange]; 12.30 (s, 1H, NH, D$_2$O exchange).

$^{13}$C NMR spectrum: δ 25.8 [CH$_3$(3)]; 28.8 [CH$_3$(3)]; 52.1 (C-3); 66.7 [CH$_2$(2)]; 87.8 (C-8a); 99.7 (C-5); 108.7 [CH (7)]; 128.7 [CH(meta), benzoyl(5)]; 129.5 [CH(ortho), benzoyl(5)]; 131.3 [CH(para), benzoyl(5)]; 140.5 [Cq, benzoyl(5)]; 147.2 [CH(6)]; 167.9 (C-4a); 191.2 [CO (8)]; 193.7 [CO, benzoyl(5)].

Mass spectrum (C.I.): m/z=300 (MH$^+$).

Example 16. Synthesis of [(RS)-3, 3-bis-(hydroxymethyl )-8a-hydroxy-8-oxo-3, 4, 8, 8a-tetrahydro-2H-1,4-benzoxazin-5-yl] ethanone (compound no. 13).

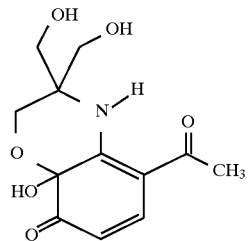
(compound no. 13)

The procedure is analogous to that described in Example 8 a), but starting with 0.34 g of 2,3,4-trihydroxyacetophenone. After purification by chromatography on a 20 g silica gel column (diameter: 1.8 cm, height 60 cm), eluted with an ethyl acetate/methanol mixture (95/5 by volume), 0.08 g of [(RS)-3,3-bis-(hydroxymethyl)-8a-hydroxy-8-oxo-3,4,8,8a-tetrahydro-2H-1,4-benzoxazin-5-yl] ethanone is obtained, in the form of an orange powder.

$^1$H NMR spectrum: δ 2.20 (s, 3H, CH$_3$); 3.35 [dd, 1H, CH$_2$OH(3), J=11 Hz, J=4 Hz]; 3.40 [d, 2H, CH$_2$OH(3), J=4 Hz]; 3.55 [dd, 1H, CH$_2$OH(3), J=11 Hz, J=4 Hz]; 3.80 [d, 1H, CH$_2$(2), J=11 Hz]; 4.15 [d, 1H, CH$_2$(2), J=11 Hz]; 5.30 [m, 3H, H(7), and OH(alcohol), D$_2$O exchange]; 7.55 [d, 1H, H(6), J=10 Hz]; 8.10 (s, 1H, OH(8a), D$_2$O exchange]; 11.90 [s, 1H, NH, D$_2$O exchange].

$^{13}$C NMR spectrum: δ 27.6 (CH$_3$); 57.3 [CH$_2$(2)]; 59.6 (C-3); 61.9 [CH$_2$OH(3)]; 62.3 [CH$_2$OH(3)]; 87.6 (C-8a); 100.8 (C-5); 109.0 [CH(7)]; 146.9 [CH(6)]; 166.0 (C-4a); 191.6 [CO(8)]; 196.0 [CO, ethanone].

Mass spectrum (C.I.): m/z=270 (MH$^+$).

Example 17. Synthesis of (RS)-3,3-bis-(hydroxymethyl)-8a-hydroxy-8-oxo-3,4,8,8a-tetrahydro-2H-1,4-benzoxazine-5-methyl carboxylate (compound no. 14).

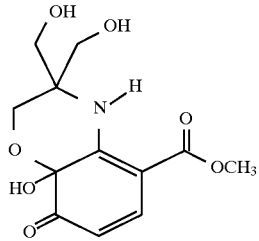
(compound no. 14)

The procedure is analogous to that described in Example 8 a), but starting with 0.37 g of 2,3,4-trihydroxyphenyl-1-methyl carboxylate (compound VIIIf described in Example 6). After purification by chromatography on a 20 g silica gel column (diameter: 1.8 cm, height 60 cm), eluted with an ethyl acetate/methanol mixture (95/5 by volume), 0.12 g of (RS)-3,3-bis-(hydroxymethyl)-8a-hydroxy-8-oxo-3,4,8,8a-tetrahydro-2H-1,4-benzoxazine-5-methyl carboxylate is obtained in the form of an orange powder.

$^1$H NMR spectrum: δ 3.30 [dd, 1H, CH$_2$OH(3), J=11 Hz, J=5 Hz]; 3.40 [d, 2H, CH$_2$OH(3), J=5 Hz]; 3.55 [dd, 1H, CH$_2$OH(3), J=11 Hz, J=5 Hz]; 3.70 (s, 3H, OCH$_3$); 3.80 [d, 1H, CH$_2$(2), J=12 Hz]; 4.15 [d, 1H, CH$_2$(2), J=12 Hz]; 5.30 [m, 3H, H(7), and OH(alcohol), D$_2$O exchange]; 7.45 [d, 1H, H(6), J=10 Hz]; 8.05 (s, 1H, OH(8a), D$_2$O exchange]; 10.00 [s, 1H, NH, D$_2$O exchange].

$^{13}$C NMR spectrum: δ 52.0 (OCH$_3$); 57.2 (C-3); 59.7 [CH$_2$(2)]; 62.0 [CH$_2$OH(3)]; 62.3 [CH$_2$OH(3)]; 87.9 (C-8a); 90.0 (C-5); 109.8 [CH(7)]; 144.7 [CH(6)]; 165.4 (C-4a); 168.1 [CO, methyl carboxylate]; 191.9 [CO(8)].

Mass spectrum (C.I.): m/z=286 (MH$^+$).

Example 18. Synthesis of [(RS)-3,3-bis-(hydroxymethyl)-8a-hydroxy-8-oxo-3,4,8,8a-tetrahydro-2H-1,4-benzoxazin-5-yl] chloroethanone (compound no. 15).

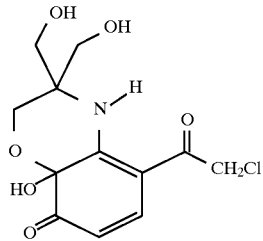
(compound no. 15)

Operating as in Example 8 b-1), but starting with 0.093 g of (3,4-dihydroxy) chloroacetophenone, 0.015 g of [(RS)-3,3-bis-(hydroxymethyl)-8a-hydroxy-8-oxo-3,4,8,8a-tetrahydro-2H-1,4-benzoxazin-5-yl] chloroethanone is thus obtained in the form of an orange powder.

$^1$H NMR spectrum: δ 3.35 [d, 1H, CH$_2$OH(3), J=11 Hz]; 3.40 [s, 2H, CH$_2$OH(3)]; 3.55 [d, 1H, CH$_2$OH(3), J=11 Hz,]; 3.85 [d, 1H, CH$_2$(2), J=11 Hz]; 4.15 [d, 1H, CH$_2$(2), J=11 Hz]; 4.60 [d, 2H, CH$_2$Cl), J=7 Hz]; 5.30 [d, 1H, H(7), J=10 Hz]; 5.40 [broad s, 2H, OH(alcohol), D$_2$O exchange]; 7.50 [d, 1H, H(6), J=10 Hz]; 8.25 (s, 1H, OH(8a), D$_2$O exchange]; 11.90 [s, 1H, NH, D$_2$O exchange].

Mass spectrum (C.I.): m/z=304 (MH$^+$).

C) Synthesis of the compounds of general formula (III)

Example 19. Synthesis of [3,3-bis-(hydroxymethyl)-8-hydroxy-3,4-dihydro-2H-1,4-benzoxazin-5-yl][phenyl] methanone (compound no. 9).

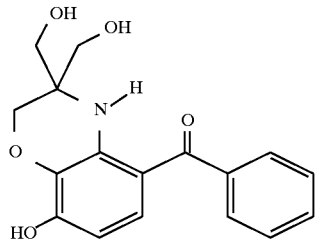
(compound no. 9)

Compound no. 9 can be prepared by controlled-potential electrolysis of compound no. 1. The electrolysis device is identical to that described in Example 8 b-1), except for the work electrode which is replaced by a sheet of mercury.

The electrolysis is carried out of a solution of 0.16 g of compound no. 1, in 250 cm$^3$ of methanol containing 2.3 g of tetraethylammonium perchlorate as support electrode, under a nitrogen atmosphere, at 25° C., at a mercury cathode whose potential is fixed at −1.5 V e.c.s. At the end of the electrolysis, when the intensity of the current has become negligible (0.5 mA) compared with the intensity of the initial current (80 mA), the resultant solution is evaporated to dryness under reduced pressure (2.7 kPa), at a temperature close to 40° C. The residue is taken up in 50 cm$^3$ of a molar aceto-acetic buffer solution the pH of which is about 4.5. The resultant solution is then extracted with 100 cm$^3$ of ethyl acetate. The combined organic phases are dried over anhydrous sodium sulphate, filtered and the solvent is evaporated to dryness under reduced pressure (2.7 kPa), at a temperature close to 40° C. After purification by chromatography on a 10 g silica gel column (diameter 1.3 cm, height 60 cm), eluted with ethyl acetate, 0.13 g of compound [3,3-bis-(hydroxymethyl)-8-hydroxy-3,4-dihydro-2H-1,4-benzoxazin-5-yl][phenyl] methanone is obtained in the form of a yellow powder melting at around 90° C. (with decomposition).

$^1$H NMR spectrum: δ 3.30 [dd, 2H, CH$_2$OH(3), J=10 Hz, J=4 Hz]; 3.45 [dd, 2H, CH$_2$OH(3), J=10 Hz, J=4 Hz]; 3.90 [s, 1H, CH$_2$(2)]; 5.00 [t, 2H, OH(alcohol), J=4 Hz, D$_2$O exchange]; 6.05 [d, 1H, H(7), J=9 Hz]; 6.80 (d, 1H, H(6), J=9 Hz]; 7.50 (m, 5H, phenyl); 8.80 [s, 1H, NH, D$_2$O exchange]; 9.90 [s, 1H, OH(8), D$_2$O exchange].

$^{13}$C NMR spectrum: δ 56.5 (C-3); 61.2 [CH$_2$OH(3)]; 65.7 [CH$_2$(2)]; 105.2 [CH(7)]; 111.2 (C-5); 129.2 [CH(ortho and meta), phenyl]; 129.7 [CH(6)]; 130.2 (C-8a); 131.3 [CH (para), phenyl]; 141.0(Cq, phenyl); 141.7 (C-4a); 150.8 (C-8); 197.0 [CO, methanone].

Mass spectrum (C.I.): m/z=316 (MH$^+$).

Example 20. Synthesis of [3,3-bis-(hydroxymethyl)-8-methoxy-3,4-dihydro-2H-1,4-benzoxazin-5-yl][phenyl] methanone (compound no. 10).

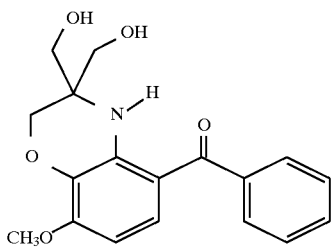
(compound no. 10)

The procedure is analogous to that described in Example 13, but starting with 0.16 g of compound no. 9. After purification by chromatography on a 10 g silica gel column (diameter 1.3 cm, height 60 cm), eluted with an ethyl acetate/cyclohexane mixture (75/25 by volume), 0.13 g of [3,3-bis-(hydroxymethyl)-8-methoxy-3,4-dihydro-2H-1,4-benzoxazin-5-yl] [phenyl] methanone is obtained in the form of a yellow powder melting at around 168° C. (with decomposition).

$^1$H NMR spectrum: δ 3.35 [dd, 2H, CH$_2$OH(3), J=11 Hz, J=5 Hz]; 3.50 [dd, 2H, CH$_2$OH(3), J=11 Hz, J=5 Hz]; 3.80 [s, 3H, OCH$_3$); 3.90 [s, 2H, CH$_2$(2)]; 5.05 [t, 2H, OH(alcohol), J=5 Hz, D$_2$O exchange]; 6.35 [d, 1H, H(7), J=9 Hz]; 6.95 [d, 1H, H(6), J=9 Hz]; 7.50 (m, 5H, phenyl); 8.60 (s, 1H, NH, D$_2$O exchange).

$^{13}$C NMR spectrum: δ 56.3 (C-3); 56.7 (CH$_3$); 61.1 [CH$_2$OH(3)]; 65.6 [CH$_2$(2)]; 100.6 [CH(7)]; 112.6 (C-5); 129.2 and 129.3 [CH(ortho and meta), phenyl]; 129.6 [CH(6)]; 131.4 (C-8a); 131.6 [CH(para), phenyl]; 140.0 (C-4a); 141.3 (Cq, phenyl); 152.3 (C-8); 197.0 [CO, methanone].

Mass spectrum (C.I.): m/z=330 (MH$^+$).

Example 21. Synthesis of [3,3-bis-(hydroxymethyl)-8-hydroxy-3,4-dihydro-2H-1,4-benzoxazin-5-yl ][3',5'-dihydroxy-4'-(2-oxo-2-phenylethoxy) phenyl] methanone (compound no. 11).

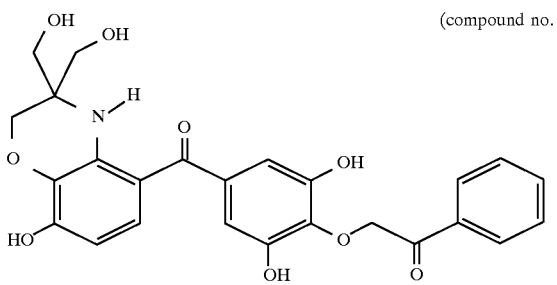
(compound no. 11)

0.58 g of compound no. 2 is dissolved in 25 cm$^3$ of a solution of glacial acetic acid diluted to the quarter in methanol. 0.38 g of zinc powder is then added in 5 minutes, at ambient temperature. The reaction mixture is stirred for 2 minutes. After filtration, 20 cm$^3$ of distilled water are added. The resultant solution is concentrated to 10 cm$^3$, under reduced pressure (2.7 kPa), at a temperature close to 40° C. The cooling of the reaction mixture brings with it the precipitation of a product which is washed with water and recrystallized from a dichloro-methane/acetone mixture (98/2 by volume). 0.39 g of [3,3-bis-(hydroxymethyl)-8-hydroxy-3,4-dihydro-2H-1,4-benzoxazin-5-yl] [3',5'-dihydroxy-4'-(2-oxo-2-phenylethoxy) phenyl] methanone is obtained in the form of a bright yellow powder melting at around 270° C. (with decomposition).

$^1$H NMR spectrum: δ 3.35 [dd, 2H, CH$_2$OH(3), J=11 Hz, J=5 Hz]; 3.50 [dd, 2H, CH$_2$OH(3), J=11 Hz, J=5 Hz]; 3.90 [s, 2H, CH$_2$(2)]; 3.95 [d, 1H, CH$_2$(phenylethoxy), J=11 Hz]; 4.20 [d, 1H, CH$_2$(phenylethoxy), J=11 Hz]; 5.05 [t, 2H, OH(alcohol) J=5 Hz, D$_2$O exchange]; 6.10 [d, 1H, H(7), J=9 Hz]; 6.60 [m, 2H, H(2') and H(6')]; 7.00 [d, 1H, H(6), J=9 Hz]; 7.40 to 7.60 (m, 5H, aromatics, phenylethoxy]; 8.55 [s, 1H, NH, D$_2$O exchange]; 9.60 [s, 2H, OH(3') and OH(5'), D$_2$O exchange]; 9.85 (s, 1H, OH(8), D$_2$O exchange).

$^{13}$C NMR spectrum: δ 56.5 (C-3); 61.3 [CH$_2$OH(3)]; 65.8 [CH$_2$(2)]; 71.3 [CH$_2$(phenylethoxy)]; 95.2 (Cq, phenylethoxy); 104.9 [CH(7)]; 110.2 and 110.6 [CH(2') and CH(6')]; 111.4 (C-5); 127.5 [CH(meta), phenylethoxy]; 129.4 [CH(ortho and para), phenylethoxy ]; 130.0 [CH(6)]; 130.4 (C-8a); 133.9 (C-4'); 134.6 (C-1'); 140.7 (C-4a); 141.1 and 143.3 (C-3' and C-5'); 146.6 (CO, phenylethoxy); 150.6 (C-8); 196.1 (CO, methanone). Mass spectrum (C.I.): m/z= 482 (MH$^+$).

Example 22. Synthesis of [3,3-bis-(hydroxymethyl)-8-hydroxy-3,4-dihydro-2H-1,4-benzoxazin-5-yl] [3',4',5'-trihydroxy-phenyl] methanone (compound no. 12).

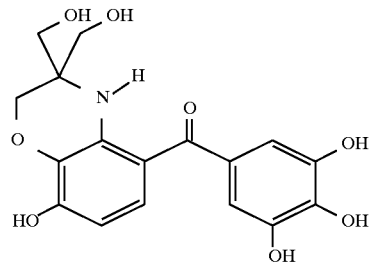
(compound no.12)

0.56 g of compound no. 2 is dissolved in 25 cm$^3$ of a solution of glacial acetic acid diluted to the quarter in methanol. 0.38 g of zinc powder is then added in 5 minutes, at ambient temperature. The reaction mixture is stirred for 30 minutes. After filtration, 20 cm$^3$ of distilled water are added. The resultant solution is concentrated to 20 cm$^3$ under reduced pressure (2.7 kPa), at a temperature close to 40° C., then extracted with 100 cm$^3$ of ethyl acetate. The combined organic phases are dried over anhydrous sodium sulphate then filtered; the ethyl acetate is evaporated to dryness under reduced pressure (2.7 kPa) at 40° C. The residue, recrystallized from a dichloro-methane/acetone mixture (95/5 by volume) allows 0.29 g of [3,3-bis-(hydroxymethyl)-8-hydroxy-3,4-dihydro-2H-1,4-benzoxazin-5-yl] [3',4',5'-trihydroxyphenyl] methanone to be obtained in the form of a yellow powder melting at around 150° C. (with decomposition).

$^1$H NMR spectrum: δ 3.30 [dd, 2H, CH$_2$OH(3), J=11 Hz, J=5 Hz]; 3.50 [dd, 2H, CH$_2$OH(3), J=11 Hz, J=5 Hz]; 3.90 [s, 2H, CH$_2$(2)]; 5.00 [t, 2H, OH(alcohol), J=5 Hz, D$_2$O exchange]; 6.10 [d, 1H, H(7), J=9 Hz]; 6.50 [s, 2H, H(2') and H(6')]; 7.00 [d, 1H, H(6), J=9 Hz]; 8.30 [s, 1H, NH, D$_2$O exchange]; 8.70 [s, 1H, OH(4'), D$_2$O exchange]; 9.15 [s, 2H, OH(3') and OH(5'), D$_2$O exchange]; 9.70 (s, 1H, OH(8), D$_2$O exchange).

$^{13}$C NMR spectrum: δ 56.3 (C-3); 61.3 [CH$_2$OH(3)]; 65.9 [CH$_2$(2)]; 104.5 [CH(7)]; 109.7 [CH(2') and CH(6')]; 111.9 (C-5); 129.2 [CH(6)]; 130.4 (C-8a); 131.5 (C-1'); 137.4 (C-4a); 140.2 (C-4'); 146.3 (C-3' and C-5'); 150.2 (C-8); 196.5 (CO, methanone).

Mass spectrum (C.I.): m/z=364 (MH$^+$).

II. Pharmacological study

The production of free radicals is implicated in the process of normal or pathological senescence and in the pathologies which are frequently associated with them: PARKINSON's disease, ALZHEIMER's disease, cerebral ischemia and hypoxia.

The literature abounds in publications establishing a link between free radicals (and NO -nitric oxide in particular) and the damage caused to the cerebral cells. Let us quote some representative publications:

- Ted. M. DAWSON, Valiona L. DAWSON, Solomon H. SNYDER. A novel neuronal messenger molecule in brain: the free radical, nitric oxide. Ann. Neurol. 1992; 32: 297–311.
- C. JEANDEL, M. B. NICOLAS, F. DUBOIS, F. NABET-BELLEVILLE, F. PENIN, G. CUNY. Lipid peroxidation and free radical scavengers in Alzheimer's disease. Gerontology, 1989; 35: 275–282.
- V. E. KAGAN et al. Antioxidant protection of the brain against oxidative stress, in FREE RADICALS IN THE BRAIN, Springer-Verlag-Berlin, 1992, 49–61.
- James B. LOHR. Oxygen radicals and neuropsychiatric illness—some speculations. Arch. gen. psychiatry, 1991, 48: 1097–1106.
- L. PACKER. Free radicals scavengers and antioxidants in prophylaxy and treatment of brain disease in FREE RADICALS IN THE BRAIN, Springer-Verlag-Berlin, 1992, 1–20.
- P. M. SINET, I. CEBALLOS-PICOT. Role of free radicals in Alzheimer's disease and Down's syndrome in FREE RADICALS IN THE BRAIN, Springer-Verlag Berlin, 1992, 91–98.
- Solomon SNYDER, David BREDT. Les fonctions biologiques du monoxyde d'azote. Pour la Science, no. 177, July 1992, 70–77.

The cytotoxic action of alloxan, at the root of the creation of the alloxan diabetes test described below, is usually associated with an excessive production of oxygenated free radicals: HO , O$_2$, H$_2$O$_2$. This finding is moreover corroborated by the fact that the diabetogenic action of alloxan is prevented by enzymes (catalase, superoxide dismutase) or reagents (alcohols, DMSO, dimethylurea, thiourea, vitamin E, vitamin C, . . .) which capture free radicals.

It is consequently recognized that a substance capable of opposing the appearance of alloxan diabetes has antiradical properties.

Using this model on rats, BENTUE-FERRER et al. (Fundam. Clin. Pharmacol. 1989, 3, 323–328) showed that exifone exerts marked antiradical properties after intravenous administration.

The alloxan diabetes test on rats, as described below, was used to study the antiradical properties of the compounds MBF 378, MBF 379, and MBF 380 (corresponding respectively to compounds no. 2, no. 11 and no. 12 of the invention and described above), compared with Exifone.

A) Material and Methods animals

The experiments were carried out on male Wistar rats weighing between about 180 g and about 200 g at the start of the experiments.

description of experiments.

The animals were deprived of food for 18 hours prior to intravenous (i.v.) injection of alloxan, and fed three hours after this injection.

On the first day of the experiment, the animals were lightly anaesthetized with ether. They then received an i.v. injection of alloxan at the rate of 40 mg/kg, then, 30 seconds later, an injection of the tested compound or of the vehicle.

On the second day, i.e. 24 hours later, the animals were anaesthetized again (using the same procedure), and received a second i.v. injection of the tested compound or of the vehicle.

A blood sample was taken 1 hour before the injection of alloxan, i.e. before the anaesthesia on the first day. A second blood sample was taken 48 hours after the injection of alloxan, i.e. 24 hours after the second injection of the tested compound or of the vehicle.

treatments

The rats were chosen at random to undergo the following different treatments:

1: control group (10 rats) treated with alloxan and NaCl (Table 1)

2: control group (10 rats) treated with alloxan and polyethylene glycol 300 (PEG 300) (Table 2)

3: group (13 rats) treated with alloxan and Exifone 60 mg/kg (Table 3)

4: group (10 rats) treated with alloxan and MBF 378 60 mg/kg (Table 4)

5: group (10 rats) treated with alloxan and MBF 379 60 mg/kg (Table 5)

6: group (10 rats) treated with alloxan and MBF 380 60 mg/kg (Table 6)

7: group (10 rats) treated with alloxan and MBF 378 30 mg/kg (Table 7)

8: group (10 rats) treated with alloxan and MBF 379 30 mg/kg (Table 8)

9: group (10 rats) treated with alloxan and MBF 380 30 mg/kg (Table 9)

10: group (4 rats) treated with alloxan and MBF 379 15 mg/kg (Table 10)

The tested compounds were injected in one go at the rate of 0.2 ml/100 g body weight in each case. They were dissolved in a mixture of PEG 300 (Sigma) and distilled water (50% aqueous solution).

glucose determination

The 1.5 ml blood samples were collected in tubes containing heparin. The plasmatic glucose (g/l) was determined by the fluorescence polarization technique (TDX Abbott).

B) Results

The results are presented in the following Tables 1 to 11 (Table 11 representing the average of the results obtained with the different groups 1 to 10 studied).

Alloxan induces a very significant increase in the plasmatic levels of glucose in the groups treated with NaCl (Table 1:0.46±0.05 g/l before injection of alloxan, as against 5.13±0.28 g/l after injection of alloxan), or with PEG 300 (Table 2:0.51±0.05 g/l before injection of alloxan, as against 4.43±0.30 g/l after injection of alloxan).

The other groups treated also showed a significant increase in the plasmatic levels of glucose. Exifone (Table 3:1.29±0.06 g/l), and the three derivatives MBF 378 (Table 4:1.35±0.02 g/l), MBF 379 (Table 5:1.28±0.04 g/l), and MBF 380 (Table 6:1.66±0.20 g/l), at the rate of 60 mg/kg, as well as the compound MBF 379 at the rate of 30 mg/kg (Table 8:1.85±0.39 g/l), permitted a very significant reduction of the diabetes induced by alloxan in the different groups studied. At a lower level, MBF 378 and MBF 380 at the rate of 30 mg/kg also proved to be effective protectors against alloxan diabetes (Table 7:3.42±0.36 g/l, and Table 9:4.04±0.36 g/l, respectively).

It should also be noted that PEG 300 does not significantly modify the effects of alloxan (Table 2:4.43±0.30 g/l, Table 1:5.13±0.28 g/l, respectively).

In conclusion, the protective effects of Exifone and of the three compounds studied in the above test are due to their power as captors of free radicals. If account is taken of the ratios of the molecular weights of these three compounds MBF 378, MBF 379 and MBR 380 to the molecular weight of Exifone (namely: 1.78, 1.73 and 1.30, respectively), it can be concluded from this that these three compounds are more active than Exifone, and that MBF 397 is the most active compound among those studied.

TABLE 1

| RAT | Glycemia (g/l) | |
|---|---|---|
| | Before alloxan | After alloxan |
| 1 | 0.48 | 6.91 |
| 2 | 0.58 | 5.68 |
| 3 | 0.48 | 5.43 |
| 4 | 0.52 | 4.63 |
| 5 | 0.26 | 4.07 |
| 6 | 0.20 | 4.54 |
| 7 | 0.32 | 5.98 |
| 8 | 0.48 | 4.30 |
| 9 | 0.55 | 4.65 |
| 10 | 0.74 | 5.07 |
| M ± SEM | 0.46 ± 0.05 | 5.13 ± 0.28 |

Glycernia values 1 h before and 48 h after i.v. injection of 40 mg/kg alloxan in rats.
NaCl 9°/oo control group. Individual results.
Mean (M) ± standard error of the mean (SEM)

TABLE 2

| RAT | Glycemia (g/l) | |
|---|---|---|
| | Before alloxan | After alloxan |
| 1 | 0.67 | 2.23 |
| 2 | 0.69 | 5.27 |
| 3 | 0.53 | 5.22 |
| 4 | 0.53 | 5.46 |
| 5 | 0.32 | 4.06 |
| 6 | 0.35 | 3.76 |
| 7 | 0.74 | 4.22 |
| 8 | 0.39 | 4.67 |
| 9 | 0.40 | 4.69 |
| 10 | 0.49 | 4.71 |
| M ± SEM | 0.51 ± 0.05 | 4.43 ± 0.30 |

Glycemia values 1 h before and 48 h after i.v. injection of 40 mg/kg alloxan in rats.
PEG 300 control group - Individual results.
Mean ± standard error of the mean.

TABLE 3

| RAT | Glycemia (g/l) | |
|---|---|---|
| | Before alloxan | After alloxan |
| 1 | 0.84 | 1.33 |
| 2 | 0.80 | exitus |
| 3 | 0.98 | 1.43 |
| 4 | 0.82 | 1.31 |
| 5 | 0.83 | exitus |
| 6 | 0.51 | 1.52 |
| 7 | 0.34 | 1.40 |
| 8 | 0.37 | 0.93 |

TABLE 3-continued

| RAT | Glycemia (g/l) | |
|---|---|---|
| | Before alloxan | After alloxan |
| 9 | 0.34 | exitus |
| 10 | 0.32 | 1.17 |
| 11 | 0.42 | exitus |
| 12 | 0.70 | exitus |
| 13 | 0.76 | 1.22 |
| M ± SEM | 0.62 ± 0.07 | 1.29 ± 0.06 |

Glycemia values 1 h before and 48 h after i.v. injection of 40 mg/kg alloxan in rats.
Exifone 60 mg/kg i.v. group - Individual results.
Mean ± standard error of the mean

TABLE 4

| RAT | Glycemia (g/l) | |
|---|---|---|
| | Before alloxan | After alloxan |
| 1 | 0.52 | 1.20 |
| 2 | 0.68 | 1.39 |
| 3 | 0.87 | 1.33 |
| 4 | 0.80 | 1.44 |
| 5 | 0.67 | 1.35 |
| 6 | 0.31 | 1.32 |
| 7 | 0.38 | 1.32 |
| 8 | 0.29 | 1.36 |
| 9 | 0.41 | 1.42 |
| 10 | 0.29 | 1.39 |
| M ± SEM | 0.52 ± 0.07 | 1.35 ± 0.02 |

Glycemia values 1 h before and 48 h after i.v. injection of 40 mg/kg alloxan in rats.
MBF 378 60 mg/kg i.v. group - Individual results.
Mean ± standard error of the mean

TABLE 5

| RAT | Glycemia (g/l) | |
|---|---|---|
| | Before alloxan | After alloxan |
| 1 | 0.40 | 1.38 |
| 2 | 0.39 | 1.39 |
| 3 | 0.50 | 1.31 |
| 4 | 0.50 | 1.45 |
| 5 | 0.31 | 1.37 |
| 6 | 0.46 | 1.34 |
| 7 | 0.32 | 1.20 |
| 8 | 0.45 | 1.08 |
| 9 | 0.36 | 1.04 |
| 10 | 0.37 | 1.27 |
| M ± SEM | 0.41 ± 0.02 | 1.28 ± 0.04 |

Glycemia values 1 h before and 48 h after i.v. injection of 40 mg/kg alloxan in rats.
MBF 379 60 mg/kg i.v. group - Individual results.
Mean ± standard error of the mean

TABLE 6

| RAT | Glycemia (g/l) | |
|---|---|---|
| | Before alloxan | After alloxan |
| 1 | 0.30 | 1.44 |
| 2 | 0.39 | 1.54 |
| 3 | 0.34 | 1.66 |
| 4 | 0.43 | 1.30 |
| 5 | 0.35 | 1.28 |
| 6 | 0.67 | 1.36 |
| 7 | 0.42 | 1.46 |

TABLE 6-continued

| RAT | Glycemia (g/l) | |
|---|---|---|
| | Before alloxan | After alloxan |
| 8 | 0.65 | 1.78 |
| 9 | 0.51 | 3.37 |
| 10 | 0.39 | 1.45 |
| M ± SEM | 0.44 ± 0.04 | 1.66 ± 0.20 |

Glycemia values 1 h before and 48 h after i.v. injection of 40 mg/kg alloxan in rats.
MBF 380 60 mg/kg i.v. group - Individual results.
Mean ± standard error of the mean

TABLE 7

| RAT | Glycemia (g/l) | |
|---|---|---|
| | Before alloxan | After alloxan |
| 1 | 0.32 | 1.10 |
| 2 | 0.29 | 2.61 |
| 3 | 0.38 | 3.91 |
| 4 | 0.42 | 2.74 |
| 5 | 0.33 | 3.08 |
| 6 | 0.31 | 2.84 |
| 7 | 0.63 | 4.44 |
| 8 | 0.53 | 4.63 |
| 9 | 0.53 | 4.60 |
| 10 | 0.81 | 4.26 |
| M ± SEM | 0.45 ± 0.05 | 3.42 ± 0.36 |

Glycemia values 1 h before and 48 h after i.v injection of 40 mg/kg alloxan in rats.
MBF 378 30 mg/kg i.v. group - Individual results.
Mean ± standard error of the mean

TABLE 8

| RAT | Glycemia (g/l) | |
|---|---|---|
| | Before alloxan | After alloxan |
| 1 | 0.28 | 1.07 |
| 2 | 0.64 | 1.29 |
| 3 | 0.31 | 1.18 |
| 4 | 0.31 | 1.20 |
| 5 | 0.44 | 1.27 |
| 6 | 0.52 | 1.09 |
| 7 | 0.52 | 4.36 |
| 8 | 0.61 | 4.04 |
| 9 | 0.51 | 1.42 |
| 10 | 0.85 | 1.59 |
| M ± SEM | 0.50 ± 0.06 | 1.85 ± 0.39 |

Glycemia values 1 h before and 48 h after i.v. injection of 40 mg/kg alloxan in rats.
MBF 379 30 mg/kg i.v. group - Individual results.
Mean ± standard error of the mean

TABLE 9

| RAT | Glycemia (g/l) | |
|---|---|---|
| | Before alloxan | After alloxan |
| 1 | 0.34 | 3.73 |
| 2 | 0.30 | 3.76 |
| 3 | 0.34 | 4.12 |
| 4 | 0.34 | 4.68 |
| 5 | 0.63 | 4.94 |
| 6 | 0.54 | 4.81 |
| 7 | 0.51 | 1.42 |
| 8 | 0.55 | 3.05 |
| 9 | 0.59 | 4.55 |
| 10 | 0.67 | 5.38 |
| M ± SEM | 0.48 ± 0.04 | 4.04 ± 0.36 |

Glycemia values 1 h before and 48 h after i.v. injection of 40 mg/kg alloxan in rats.
MBF 380 30 mg/kg i.v. group - Individual results.
Mean ± standard error of the mean

TABLE 10

| RAT | Glycemia (g/l) | |
|---|---|---|
| | Before alloxan | After alloxan |
| 1 | 0.85 | 3.70 |
| 2 | 0.85 | 3.61 |
| 3 | 0.94 | 5.74 |
| 4 | 0.75 | 2.53 |
| M ± SEM | 0.85 ± 0.04 | 3.89 ± 0.67 |

Glycemia values 1 h before and 48 h after i.v. injection of 40 mg/kg alloxan in rats.
MBF 379 15 mg/kg i.v. group - Individual results.
Mean ± standard error of the mean

TABLE 11

| GROUP | | Glycemia (g/l) | |
|---|---|---|---|
| | | Before alloxan | After alloxan |
| Control | (NaCl 9°/oo) | 0.46 ± 0.05 | 5.13 ± 0.28 |
| Control | (PEG 300) | 0.51 ± 0.05 | 4.43 ± 0.30 |
| Exifone | 60 mg/kg | 0.62 ± 0.07 | 1.29 ± 0.06 |
| MBF 378 | 60 mg/kg | 0.52 ± 0.07 | 1.35 ± 0.02 |
| MBF 379 | 60 mg/kg | 0.41 ± 0.02 | 1.28 ± 0.04 |
| MBF 380 | 60 mg/kg | 0.44 ± 0.04 | 1.66 ± 0.20 |
| MBF 378 | 30 mg/kg | 0.45 ± 0.05 | 3.42 ± 0.36 |
| MBF 379 | 30 mg/kg | 0.50 ± 0.06 | 1.85 ± 0.39 |
| MBF 380 | 30 mg/kg | 0.48 ± 0.04 | 4.04 ± 0.36 |
| MBF 379 | 15 mg/kg | 0.85 ± 0.04 | 3.89 ± 0.67 |

Glycemia values 1 h before and 48 h after i.v. injection of 40 mg/kg alloxan in rats.
Effects of exifone and of its three derivatives.
Mean ± standard error of the mean with 10 animals per group except for exifone 60 mg/kg and MBF 379 15 mg/kg with 8 and 4 animals, respectively.

We claim:
1. A compound having the following formula (IV):

$$\text{(IV)}$$

in which:
- $R_1$ and $R_2$, independently of each other, represent an alkyl group with 1 to 3 carbon atoms, or a group formula $-CH_2-OR_a$, $R_a$ representing a hydrogen atom or a methyl group,
- $R_3$ and $R_5$, independently of each other, represent a hydrogen atom, or an $-OH$ group, or an $-OCH_3$ group,
- $R_4$ represents a hydrogen atom, or an $OR_b$ group, $R_b$ representing a hydrogen atom or a methyl group, or $R_4$ represents a group of formula $OR_c$, $R_c$ representing a group of formula —$CH_2$—CO—$C_6H_4R'$ in which R' represents a hydrogen atom, —CN or —$OCH_3$, either $R_6$ represents an $OR_d$ group, $R_d$ representing a hydrogen atom or a methyl group, when $R_7$ and $R_8$ combine to form a double bond, or $R_8$ represents an —$OR_e$ group in which $R_e$ represents a hydrogen atom or a methyl group, when $R_6$ and $R_7$ combine to form, with the carbon atom in position 8 of the ring, a C=O group.

2. The compound according to claim 1, characterized in that it corresponds to the following formula (V):

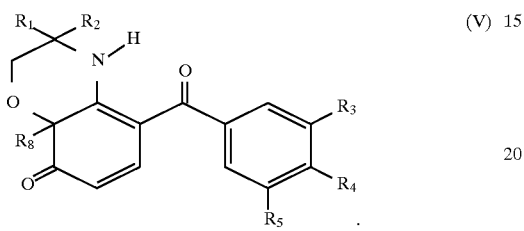
(V)

3. The compound according to claim 2, characterized in that it corresponds to the following formula:

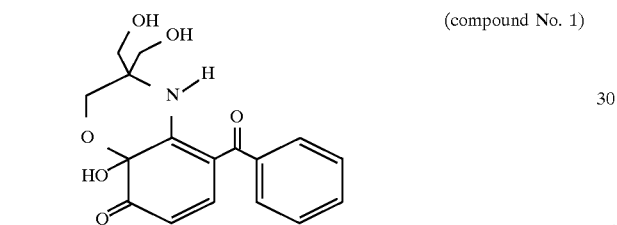
(compound No. 1)

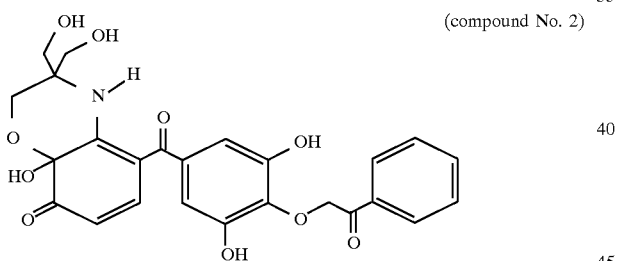
(compound No. 2)

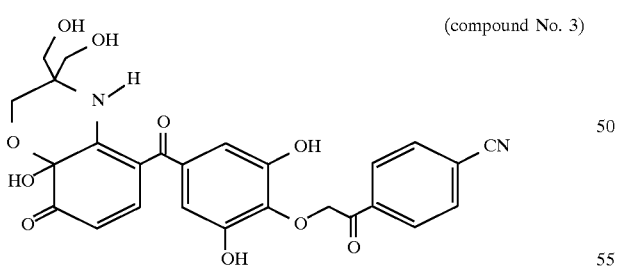
(compound No. 3)

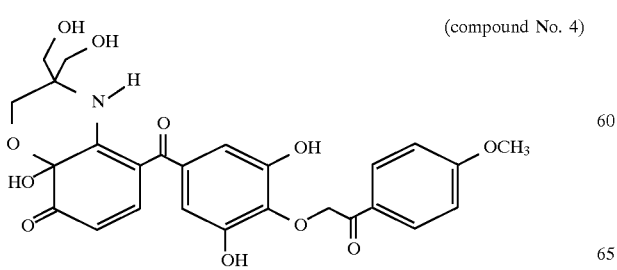
(compound No. 4)

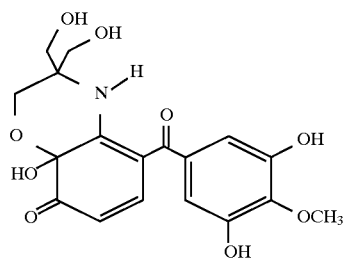
(compound No. 5)

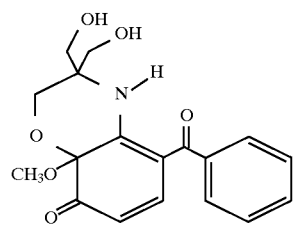
(compound No. 6)

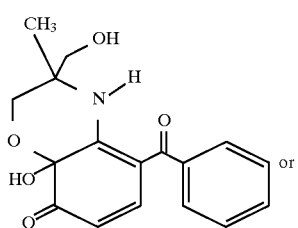
(compound No. 7)

or

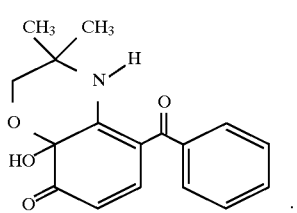
(compound No. 8)

4. The compound according to claim 1, characterized in that it corresponds to the following formula (VI):

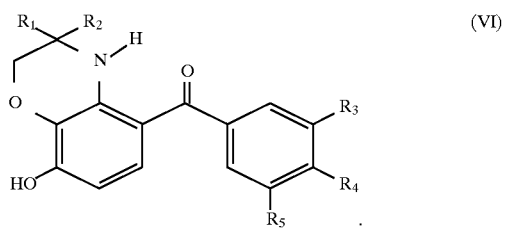
(VI)

5. The compound according to claim 4, characterized in that it corresponds to the following formnulae:

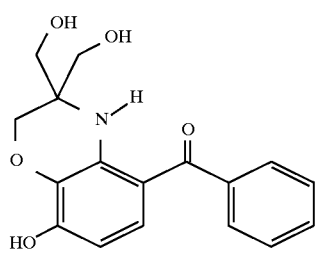
(Compound No. 9)

-continued (Compound No. 11)

(Compound No. 12)

6. The compound according to claim 1, characterized in that it corresponds to the following formulae:

(Compound No. 10)

7. Pharmaceutical composition, characterized in that it contains, as active ingredient, at least one compound according to a claim 1 in combination with a pharmaceutically acceptable vehicle.

8. The pharmaceutical composition according to claim 7, characterized in that it can be administered in a form selected from the group consisting essentially of orally in the form of tablets, orally in the form of capsules, parenterally in the form of an intravenous injection, parenterally in the form of an intramuscular injection and parenterally in the form of a subcutaneous injection.

9. The pharmaceutical composition according to claim 8, characterized in that the daily posology for the oral forms is from about 3 mg/kg to about 20 mg/kg and in that the daily posology for the parenteral forms is from about 1 mg/kg to about 5 mg/kg.

10. The pharmaceutical composition according to claim 7, characterized in that the unit doses of active ingredient, depending on the different forms of presentation of the said composition, are as follows:

oral form: about 1 mg/kg to about 10 mg/kg, parenteral form: about 0.3 mg/kg to about 1 mg/kg.

11. The pharmaceutical composition according to claim 9 wherein the daily posology for oral forms is about 15 mg/kg.

12. The pharmaceutical composition according to claim 10 wherein the unit dose for the oral form is about 5 mg/kg.

13. A method for treating one of a cognitive disorder and a cerebral affection which may be due to, maintained and/or aggravated by the presence of free radicals in the brain comprising administering an affective amount of a composition having the following formula:

in which:
—$R_1$ and $R_2$, independently of each other, represent an alkyl group with 1 to 3 carbon atoms, or a group formula —$CH_2$—$OR_a$, $R_a$ representing a hydrogen atom or a methyl group, —$R_3$ and $R_5$, independently of each other, represent a hydrogen atom, or an —OH group, or an —$OCH_3$ group, $R_4$ represents a hydrogen atom, or an $OR_b$ group, $R_b$ representing a hydrogen atom or a methyl group, or $R_4$ represents a group of formula $OR_c$, $R_c$ representing a group of formula —$CH_2$—CO—$C_6H_4R'$ in which R' represents a hydrogen atom, —CN or —$OCH_3$, either $R_6$ represents an $OR_d$ group, $R_d$ representing a hydrogen atom or a methyl group, when $R_7$ and $R_8$ combine to form a double bond, or $R_8$ represents an —$OR_e$ group in which $R_e$ represents a hydrogen atom or a methyl group, when $R_6$ and $R_7$ combine to form, with the carbon atom in position 8 of the ring, a C=O group.

14. The method according to claim 13 wherein said cognitive disorder is a memory disorder.

15. The method according to claim 13 wherein said cerebral affection is selected from the group consisting of Alzheimer's disease, Parkinson's disease, Trisomy (Down's Syndrome), schizophrenia and epilepsy.

16. A method of preparing compounds corresponding to the following formula (IV):

(IV)

in which:
—$R_1$ and $R_2$, independently of each other, represent an alkyl group with 1 to 3 carbon atoms, or a group of formula —$CH_2$—$OR_a$, $R_a$ representing a hydrogen atom or a methyl group, —$R_3$ and $R_5$, independently of each other, represent a hydrogen atom, or an —OH group, or an —$OCH_3$ group, —$R_4$ represents a hydrogen atom, or an —$OR_b$ group, $R_b$ representing a hydrogen atom or a methyl group, or $R_4$ represents a group of formula —$OR_c$, $R_c$ representing a group of formula —$CH_2$—CO—$C_6H_4R'$ in which R' represents a hydrogen atom, —CN or —$OCH_3$, either $R_6$ represents an —$OR_d$ group, $R_d$ representing a hydrogen atom or a methyl group, when $R_7$ and $R_8$ combine to form a double bond, or $R_8$ represents an —$OR_e$ group in which $R_e$ represents a hydrogen atom or a methyl group, when $R_6$ and $R_7$ combine to form, with the carbon atom in position 8 of the ring, a C=O group, comprising the following steps: treating a derivative of the following formula (VIII'):

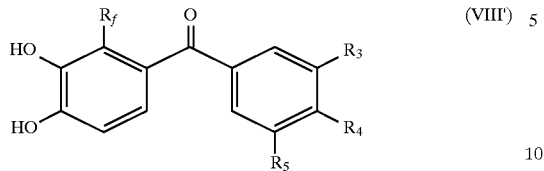

in which $R_f$ represents H or OH, and $R_3$, $R_4$, and $R_5$ are as defined above, by bringing together said derivative of formula (VIII') and a derivative of formula $NH_2$—$C(R_1,R_2)$—$CH_2OH$ in which $R_1$ and $R_2$ are as defined above, in the presence of a metal oxide selected from the group consisting essentially of $Ag_2O$, AgO and $PtO_2$, in an alcoholic medium which leads to the obtaining of a compound of the following formula (V):

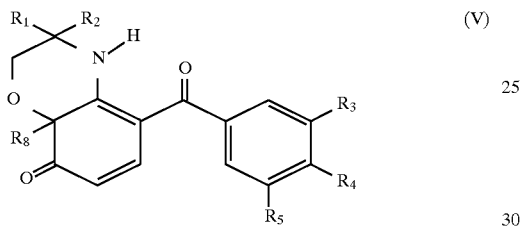

in which $R_8$ represents an —OH group, and $R_1$–$R_5$ are as defined above, on condition that when $R_4$ represents an —OH group, and at least one of the groups $R_3$ or $R_5$ represents an —OH group, which corresponds to the derivative of formula (VIII'bis), the treatment stage described above is preceded by a stage protecting the —OH group corresponding to $R_4$ of the said derivative of formula (VIII' bis), this protection stage being carried out by treatment of the derivative of formula (VIII'bis), with a derivative of formula $X^1$—$CH_3$ or $X^1$—$R_c$ in which $X^1$ represents a halogen atom, and $R_c$ is as defined above, which leads to the obtaining of a derivative of formula (VIII' ter) corresponding to a derivative of formula (VIII'bis) in which at least one of $R_3$ or $R_5$ represents —OH, whilst $R_4$ represents an —$OR_c$ group, $R_c$ having the definition indicated above, this derivative of formula (VIII' ter) then being treated in the manner indicated above by a derivative of formula $NH_2$—C$(R_1,R_2)$—$CH_2OH$ in an alcoholic medium, which leads to the obtaining of a compound of the above-mentioned formula (V) in which $R_8$ represents an —OH group, and $R_1$ and $R_2$ are as defined above, and at least one of $R_3$ or $R_5$ represents —OH, $R_4$ represents —$OCH_3$ or —$OR_c$, $R_c$ being defined above.

17. The method according to claim 16 further comprising the steps of:

either alkylation of the compound of formula (V) by treatment of this compound in a basic medium with a derivative of formula $X^2$—$CH_3$, in which $X^2$ represents a halogen atom, which leads to the obtaining of a compound of the above-mentioned formula (V) in which $R_8$ represents an —$OCH_3$ group, and $R_1$–$R_5$ are as defined above, or reduction of the compound of formula (V) by a treatment of the compound of formula (V) with an acetic acid solution in the presence of Zn at ambient temperature, which leads to the obtaining of a compound of the following formula (III'):

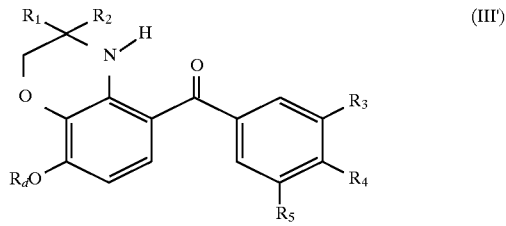

in which $R_d$ represents H, and $R_1$–$R_5$ are as defined above, on condition that when $R_4$ represents an —$OR_c$ group, $R_c$ being as defined above, and $R_3$ and $R_5$ being as defined above, the above-mentioned chemical reduction is carried out either with about five equivalents of zinc, the contact time between said compound of formula (V) and the zinc being about 2 minutes, which leads to the obtaining of a compound of the above-mentioned formula (III'), in which $R_4$ represents an —$OR_c$ group, $R_c$ being as defined above, and $R_3$ and $R_5$ being as defined above, or with about one hundred equivalents of zinc, the contact time between said compound of formula (V) and the zinc being about 10 minutes, or advantageously with about five equivalents of zinc, the above-mentioned contact time then being about 30 minutes, which leads, in these last two cases, to the obtaining of a compound of the above-mentioned formula (III') in which $R_4$, represents an —OH group, and $R_3$ and $R_5$ being as defined above.

18. The method according to claim 17 further comprising the step of alkylation of the compound of formula (III') by treatment of this compound in a basic medium with a derivative of formula $X^3$—$CH_3$, in which $X^3$ represents a halogen atom, which leads to the obtaining of a compound of the above-mentioned formula (III') in which $R_d$ represents an —$OCH_3$ group, and $R_1$–$R_5$ are as defined above.

19. The method according to claim 16 wherein the alcoholic medium is a methanolic medium.

20. The method according to claim 16 wherein the alcoholic solution is a methanolic solution.

21. The method according to claim 16 wherein the halogen atom is selected from the group consisting of iodine and bromine.

22. The method according to claim 17 wherein the halogen atom is iodine.

23. The method according to claim 16 wherein the halogen atom is iodine.

* * * * *